United States Patent [19]

Gidda et al.

[11] Patent Number: 5,216,002

[45] Date of Patent: Jun. 1, 1993

[54] METHOD OF TREATING INFLAMMATORY BOWEL DISEASE

[75] Inventors: Jaswant S. Gidda, Carmel; Jill A. Panetta, Zionsville; Michael L. Phillips, Indianapolis, all of Ind.

[73] Assignee: Eli Lilly and Company, Indianapolis, Ind.

[21] Appl. No.: 624,814

[22] Filed: Dec. 7, 1990

Related U.S. Application Data

[63] Continuation-in-part of Ser. No. 454,203, Dec. 21, 1989, abandoned.

[51] Int. Cl.$^5$ .................. A61K 31/425; A61K 31/535; A61K 21/495; A61K 31/50; C07D 277/04; C07D 277/12; C07D 277/34; C07D 327/00; C07D 333/48; C07D 417/06

[52] U.S. Cl. .................... 514/369; 514/231.5; 514/236.8; 514/252; 514/326; 514/439; 514/445; 514/446; 544/133; 544/145; 544/146; 544/369; 544/374; 546/209; 546/212; 546/213; 548/182; 548/183; 548/186; 548/187; 548/250; 548/253; 549/30; 549/40; 549/62; 549/66; 549/67

[58] Field of Search ............... 548/182, 183, 250, 253, 548/186, 187; 549/30, 40, 62, 66, 67; 514/369, 439, 445, 446, 231.5, 252, 342, 382; 544/369, 133, 145, 146, 374; 546/209, 212, 213

[56] References Cited

U.S. PATENT DOCUMENTS

| | | | |
|---|---|---|---|
| 4,287,200 | 9/1981 | Kawamatsu et al. | 424/270 |
| 4,376,777 | 3/1983 | Kawamatsu et al. | 424/270 |
| 4,387,101 | 6/1983 | Kawamatsu et al. | 424/270 |
| 4,461,902 | 7/1984 | Kawamatsu et al. | 548/183 |
| 4,464,382 | 8/1984 | Tanouchi et al. | 424/270 |
| 4,636,516 | 1/1987 | Kubo et al. | 514/365 |
| 5,136,037 | 8/1992 | Hrib et al. | 546/17 |

FOREIGN PATENT DOCUMENTS

| | | |
|---|---|---|
| 47109 | 3/1982 | European Pat. Off. . |
| 59090 | 9/1982 | European Pat. Off. . |
| 204964 | 12/1986 | European Pat. Off. . |
| 211670 | 2/1987 | European Pat. Off. . |
| 343643 | 11/1989 | European Pat. Off. . |
| 391644 | 10/1990 | European Pat. Off. . |
| 398179 | 11/1990 | European Pat. Off. . |
| 2624856A | of 0000 | Fed. Rep. of Germany . |
| 1038050 | 9/1958 | Fed. Rep. of Germany . |
| 226617 | of 0000 | U.S.S.R. . |
| 228031 | of 0000 | U.S.S.R. . |

OTHER PUBLICATIONS

Patent Abst. of Japan, 11(206), (C-433)[2653](1987), abstracting JP 60-167999.
Patent Abst. of Japan, 11(232), (C-437)[2679](1987), abstracting JP 60-184085.
Gertner et al., *Gastroent. J. Club*, 2, 3 (1990).
Teuber et al., *Liebigs Ann. Chem.*, 757 (1978).
Patent Abst. of Japan, 5(168), (C-77)[840]1981, abstracting JP 56-97277.
U.S. application Ser. No. 07/604,147, Panetta, Apr. 3, 1990.
Ito et al., *Agr. Biol. Chem.*, 29(8), 728 (1965).
Derwent 87-076383/11 abstracting J6 2029-579-A.
Isomura et al., *Chem. Pharm. Bul.*, 32(1), 152 (1984).
Hidaka et al., *Japan J. Pharmacol.*, 36(77) (1984).

(List continued on next page.)

Primary Examiner—Cecilia Tsang
Attorney, Agent, or Firm—Douglas J. Taylor; Leroy Whitaker

[57] ABSTRACT

Provided is a method of treating inflammatory bowel disease in mammals utilizing certain benzyl-substituted rhodanine derivatives. Also provided are novel benzyl-substituted rhodanine derivatives and pharmaceutical compositions thereof, as well as a novel process for selectively isolating in substantially pure enantiomeric form the enantiomers of certain racemic benzyl-substituted rhodanine derivatives.

28 Claims, No Drawings

OTHER PUBLICATIONS

Derwent 84-213508/35, abstracting Australian Patent 8423-287.
Derwent 85-113078/19, abstracting Japanese J6 0054-315-A.
Katsumi et al., *Chem. Pharm. Bul.*, 34(4), 1619 (1986).
Kagan, "Asymmetric Oxidation Mediated by Organometallic Species", *Stereochem. Org. Bioorg. Transform. Proc. Workshop Conf. Hoescht,* 17, 31 (1986) (Kagan I).
Martin et al., *J. Am. Chem. Soc.*, 103, 6237-6240 (1981).
Kitano et al., *J. Org. Chem.*, 54, 994-996 (1989).
Pitchen et al., *J. Am. Chem. Soc.*, 106, 8188-8193 (1984).
Di Furia et al., *Synthesis,* 1984, 325-326 (1984).
Kagen et al., *Pure & Appl. Chem.*, 57(12), 1911-1916 (1985) (Kagen II).
Dunach et al., *Nouv. J. Chim.*, 9(1), 1-3 (1985).
Brunner, *Synthesis,* 1988, 649 (1988).
Takata et al., *Tet. Lett.*, 27(14), 1591-1594 (1986).
Kagan et al., *Chemica Scripta,* 25, 101-103 (1985) (Kagan III).
Kagan et al., *Phosphorus and Sulfur,* 27, 127-132 (1986) (Kagan IV).
Zhao et al., *Tetrahedron,* 43(21), 5135-5144 (1987) (Zhao I).
Beckwith et al., *J. Chem Soc., Chem. Comm.*, 189-190 (1986).
Zhao et al., *C.R. Acad. Sc. Paris,* t. 304, II(7), 273-274 (1987) (Zhao II).

METHOD OF TREATING INFLAMMATORY BOWEL DISEASE

CROSS REFERENCE TO RELATED APPLICATIONS

This application is a continuation-in-part of copending application Ser. No. 07/454,203, filed Dec. 21, 1989, now abandoned.

BACKGROUND OF THE INVENTION

Mammals, both humans and animals, are known to suffer from various conditions involving inflammation of the bowels. Such conditions are typically characterized by unpleasant symptoms such as diarrhea, cramping and loss of appetite. Certain of the conditions, in particular ulcerative colitis, are also characterized by patches of ulceration. Accordingly, there is a need for a safe drug which will decrease the severity of bowel inflammation and alleviate the symptoms associated therewith.

Teuber et al., *Liebigs Ann. Chem.*, 757 (1978) discloses 5-([3,5-bis(1,1-dimethylethyl)-4-hydroxyphenyl]methylene)-2-thioxo-4-thiazolidinone as an intermediate in the preparation of certain compounds, which are in turn used for the spin-labeling of peptides. No biological activity is disclosed for this intermediate compound.

European Patent Application 211,670 discloses certain di-t-butylphenol substituted rhodanine derivatives which are useful in treating inflammation, stroke and arthritis in mammals. The inflammatory conditions which may be treated using the reference compounds involve inflammation of skin tissue and joint swelling. Such conditions are commonly associated with diseases such as rheumatoid arthritis, rheumatoid spondylitis, osteoarthritis, degenerative joint diseases and the like. Methods for treating inflammatory conditions involving inflammation of the bowels are not disclosed.

The present invention relates to a method of treating inflammatory bowel diseases. More specifically, the invention provides a method of treating inflammatory bowel diseases in humans using a benzyl substituted rhodanine derivative. The present method provides for safe and efficacious reduction in the severity of bowel inflammation, and also alleviates the unpleasant symptoms associated therewith.

SUMMARY OF THE INVENTION

The present invention provides a method of treating inflammatory bowel disease in a mammal suffering from said disease, or susceptible to said disease, comprising administering to said mammal an effective amount of a compound of the Formula (I)

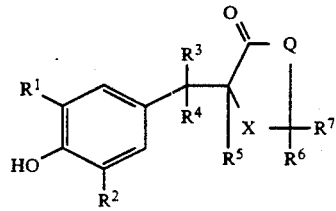

wherein:

$R^1$ and $R^2$ are each independently hydrogen, $C_1-C_6$ alkyl, $C_1-C_6$ alkoxy, $C_2-C_6$ alkenyl, $C_2-C_6$ alkynyl,

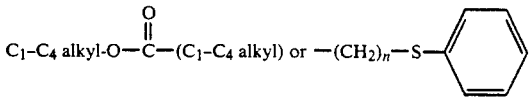

where
n is an integer from 0 to 3, both inclusive;
$R^3$ is hydrogen or $C_1-C_6$ alkyl;
$R^4$ and $R^5$ are each hydrogen or when taken together form a bond;
$R^5$ and $R^7$ are each hydrogen or when taken together are =S, or when one of $R^6$ and $R^7$ is hydrogen the other is —OH or —$SCH_3$;
X is

where m is 0, 1 or 2; and
Q is —$CH_2$, —O— or $NR^8$ where $R^8$ is hydrogen, $C_1-C_6$ alkyl, $C_2-C_6$ alkenyl, $C_3-C_8$ cycloalkyl, —$SO_2CH_3$ or —$(CH_2)_n$—Y, where n is an integer from 0 to 3, both inclusive, and Y is cyano, $OR^9$,

tetrazolyl, —$NR^{11}R^{12}$, —SH, —$S(C_1-C_4$ alkyl) or

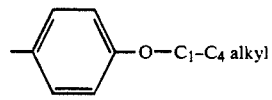

where $R^9$ is hydrogen, $C_1-C_4$ alkyl, or

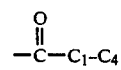

alkyl; $R^{10}$ is $C_1-C_4$ alkyl, $C_1-C_4$ alkoxy or —$NH_2$; $R^{11}$ and $R^{12}$ are each independently hydrogen, $C_1-C_6$ alkyl, $C_2-C_6$ alkenyl, $C_2-C_6$ alkynyl, —$(CH_2)_q$OH, —$(CH_2)_q$—$N(C_1-C_4$ alkyl)$_2$, —$(CH_2)_q$—$S(C_1-C_4$ alkyl) or

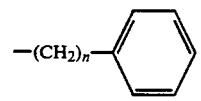

where n is as defined above and q is an integer from 1 to 6, both inclusive; or $R^{11}$ and $R^{12}$ taken together form a morpholinyl, piperidinyl, piperazinyl or an N-methylpiperazinyl ring; or a pharmaceutically acceptable salt thereof.

The present invention further provides new compounds of the Formula II

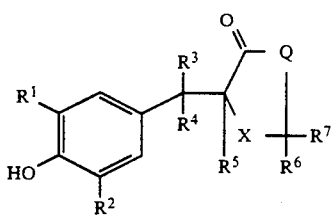 (II)

wherein:

$R^1$ is $C_2$-$C_6$ alkenyl, $C_2$-$C_6$ alkynyl or

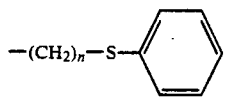

where n is an integer from 0 to 3, both inclusive; $R^2$ is hydrogen, $C_1$-$C_6$ alkyl, $C_1$-$C_6$ alkoxy, $C_2$-$C_6$ alkenyl, $C_2$-$C_6$ alkynyl,

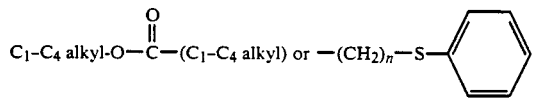

where n is as defined above; and $R^3$, $R^4$, $R^5$, $R^6$, $R^7$, X and Q are as defined for Formula I; and pharmaceutically acceptable salts thereof.

According to a further aspect of the present invention, there are provided pharmaceutical compositions comprising as active ingredient a compound of Formula II, or a pharmaceutically acceptable salt thereof, in association with one or more pharmaceutically acceptable diluents, carriers or excipients therefor.

Finally, the present invention also provides a process for selectively isolating, in substantially pure enantiomeric form, one of the enantiomers of a racemic mixture of a compound of Formula I wherein X is —S—; $R^4$ and $R^5$ are hydrogen; and $R^1$, $R^2$, $R^3$, $R^6$, $R^7$ and Q are as defined for Formula I, comprising a) reacting the racemic sulfide compound with a reagent prepared from the combination of a tartrate ligand, a titanium alkoxide, a hydroperoxide and, optionally, water until substantially all of the undesired enantiomer of the sulfide substrate has been converted to its sulfoxide analog; and b) separating the unreacted portion of the sulfide starting material, consisting essentially of substantially pure desired enantiomer, from the reaction mixture.

DETAILED DESCRIPTION OF THE INVENTION

As used herein, the term "$C_1$-$C_6$ alkyl" refers to straight and branched chain aliphatic radicals of 1 to 6 carbon atoms, both inclusive, such as methyl, ethyl, propyl, isopropyl, butyl, isobutyl, sec-butyl, tert-butyl, n-pentane, isopentane, n-hexane, isohexane and the like. The term "$C_1$-$C_6$ alkyl" includes within its definition the term "$C_1$-$C_4$ alkyl".

The term "$C_1$-$C_6$ alkoxy" refers to the alkyl radicals of 1 to 6 carbon atoms, both inclusive, attached to the remainder of the molecule by oxygen and includes methoxy, ethoxy, propoxy, isopropoxy, butoxy, isobutoxy, sec-butoxy, tert-butoxy, pentoxy, hexoxy and the like.

The term "$C_1$-$C_6$ alkoxy" includes within its definition the term "$C_1$-$C_4$ alkoxy".

The term "$C_2$-$C_6$ alkenyl" refers to straight and branched chain radicals of 2 to 6 carbon atoms, both inclusive, having a double bond. As such, the term includes ethylene, propylene, isopropylene, 1-butene, 2-butene, 2-methyl-1-propene, 1-pentene, 2-pentene, 2-methyl-2-butene and the like.

The term "$C_2$-$C_6$ alkynyl" refers to straight and branched chain radicals of 2 to 6 carbon atoms, both inclusive, having a triple bond. As such , the term includes acetylene, propyne, 1-butyne, 2-butyne, 1-pentyne, 2-pentyne, 3-methyl-1-butyne, 1-hexyne, 2-hexyne, 3-hexyne and the like.

Compounds of Formula I wherein $R^1$ and $R^2$ are other than

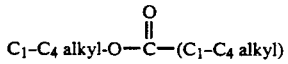

$R^8$ is other than $C_2$-$C_6$ alkenyl, Y is other than —SH or —S($C_1$-$C_4$ alkyl) and $R^{11}$ and $R^{12}$ are other than $C_2$-$C_6$ alkenyl or $C_2$-$C_6$ alkynyl are preferred for use in the method of treating inflammatory bowel disease of the present invention. Of this preferred group of compounds, somewhat more preferred are those compounds of Formula I wherein $R^1$ and $R^2$ are each $C_1$-$C_4$ alkyl, $C_2$-$C_6$ alkenyl, $C_1$-$C_6$ alkoxy or

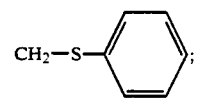

$R^3$ is hydrogen; $R^4$ and $R^5$ are each hydrogen or when taken together form a bond; $R^6$ and $R^7$ are each hydrogen or when taken together are

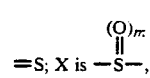

where m is 0; and Q is —O— or $NR^8$, where $R^8$ is as defined for the preferred group of compounds. Of this somewhat more preferred group of compounds, particularly preferred compounds for use in treating inflammatory bowel disease are those compounds wherein $R^1$, $R^2$, $R^3$, $R^4$, $R^5$, $R^6$, $R^7$, X and m are as set forth immediately above, and Q is $NR^8$ where $R^8$ is hydrogen, $C_1$-$C_6$ alkyl or —(CH$_2$)$_n$—Y; where n is 0 and Y is —NR$^{11}$R$^{12}$ ($R^{11}$ and $R^{12}$ each being independently hydrogen or $C_1$-$C_6$ alkyl).

Of these particularly preferred compounds, especially preferred compounds for use in the method of the present invention are those compounds wherein $R^1$ and $R^2$ are independently $C_1$-$C_6$ alkyl, in particular 1,1-dimethylethyl; $R^3$, $R^4$, $R^5$, $R^6$ and $R^7$ are hydrogen; X is

where m is 0; and Q is $NR^8$ where $R^8$ is hydrogen. The most preferred compounds for use in the method of treating inflammatory bowel disease provided by the present invention are 5-[[3,5-bis(1,1-dimethylethyl)-4- hydroxyphenyl]methyl]-4-thiazolidinone, 5-[[3-(1,1-dimethylethyl)-4-hydroxy-5-propylphenyl]methyl]-4-thiazolidinone and 5-[[3,5-dipropyl-4-hydroxyphenylmethyl]methyl]-4-thiazolidinone.

Compounds of Formula II wherein $R^2$ is other than

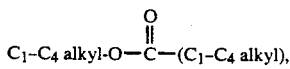
$$C_1\text{-}C_4 \text{ alkyl-O}-\overset{\overset{O}{\|}}{C}-(C_1\text{-}C_4 \text{ alkyl}),$$

$R^8$ is other than $C_2\text{-}C_6$ alkenyl, Y is other than —SH or —S($C_1\text{-}C_4$ alkyl) and $R^{11}$ and $R^{12}$ are other than $C_2\text{-}C_6$ alkenyl or $C_2\text{-}C_6$ alkynyl are preferred. Of this preferred group of compounds, somewhat more preferred are those compounds of Formula II wherein $R^1$ is $C_2\text{-}C_6$ alkenyl; $R^2$ is $C_1\text{-}C_6$ alkyl or $C_2\text{-}C_6$ alkenyl; $R^3$ is hydrogen; $R^4$ and $R^5$ are each hydrogen or when taken together form a bond; $R^6$ and $R^7$ are each hydrogen or when taken together are =S; X is

$$-\overset{\overset{(O)_m}{\|}}{S}-,$$

where m is 0; and Q is —O— or $NR^8$, where $R^8$ is as defined for the preferred group of compounds. Of this somewhat more preferred group of compounds, particularly preferred compounds are those compounds wherein $R^1$, $R^2$, $R^3$, $R^4$, $R^5$, $R^6$, $R^7$, X and m are as set forth immediately above, and Q is $NR^8$ where $R^8$ is hydrogen, $C_1\text{-}C_6$ alkyl or —$(CH_2)_n$—Y; where n is 0 and Y is —$NR^{11}R^{12}$ ($R^{11}$ and $R^{12}$ each being independently hydrogen or $C_1\text{-}C_6$ alkyl). Of these particularly preferred compounds, especially preferred compounds are those compounds wherein $R^1$ and $R^2$ are each independently $C_2\text{-}C_6$ alkenyl; $R^3$, $R^4$, $R^5$, $R^6$ and $R^7$ are hydrogen; X is

$$-\overset{\overset{(O)_m}{\|}}{S}-,$$

where m is 0; and Q is $NR^8$ where $R^8$ is hydrogen. The most preferred compound of the present invention is 5-[[3,5-di-2-propenyl-4-hydroxyphenyl]methyl]-4-thiazolidinone.

The compounds of the present invention, as well as the compounds employed in the method of the present invention, wherein $R^4$ and $R^5$ are hydrogen have an asymmetric center at the carbon atom at the 5-position of the rhodanine, or rhodanine derivative, ring. As such, the compounds can exist as either a racemic mixture, or as individual stereoisomers. The method and compounds of the present invention encompass both the racemate and its individual stereoisomers. The process of the invention provides a method for obtaining stereoisomers of certain of the compounds of the present invention, as well as certain of the compounds used in the method of the present invention.

Pharmaceutically acceptable salts are considered to be encompassed within the compounds and method of the present invention. Such salts may be prepared by reacting a compound of Formula I or II with a strong base, such as sodium hydroxide, or a strong acid such as hydrochloric acid.

Compounds of the present invention include the following:

5-[[3,5-diethenyl-4-hydroxyphenyl]methylene]-3—(3-methoxypropyl)-2-thioxo-4-thiazolidinone 5-[[3,5-bis(4-pentyne)-4-hydroxyphenyl]methyl]-3-ethylamino-4-thiazolidinone 5-[[3-ethylthiophenyl-4-hydroxy-5-methylphenyl]methylene]-2-thioxo-4-thiazolidinone 5-[[3—(2-butene)-4-hydroxy-5-isopropoxyphenyl]methyl]-3—(3-diethylaminopropyl)-4-thiazolidinone 5-[[3—(2-propenyl)-4-hydroxy-5—(1,1-dimethylethyl)-phenylmethylene]-3-cyclohexyl-4-thiazolidinone 5-[[3,5—(methylthiophenyl)-4-hydroxyphenyl]methylene]-3-propyl-2-thioxo-4-thiazolidinone 5-3,5-diacetylene-4-hydroxyphenyl]methyl]-4-thiazolidinone 5-[[3—(3-methyl-1-butene)-4-hydroxy-5-propylphenyl]methylene]-3-ethylcyano-4-thiazolidinone 5-[[3—(2-propenyl)-4-hydroxy-5-methoxyphenylmethyl]-3-ethoxy-4-thiazolidinone 5-[[3,5-di-2-propenyl)-4-hydroxyphenyl]methylene]-3—(methylaminomethyl)-2-thioxo-4-thiazolidinone The following compounds illustrate representative compounds, in addition to those mentioned above, which are suitable for use in the method of the present invention.

5-[[3,5-bis(1,1-dimethylethyl)-4-hydroxyphenylmethylene]-3—(3-methoxypropyl)-2-thioxo-4-thiazolidinone 5-[[3,5-bis(1,1-dimethylethyl)-4-hydroxyphenyl]methylene]-2-thioxo-4-thiazolidinone 5-[[3,5-bis(1,1-dimethylethyl)-4-hydroxyphenyl]methylene]-4-thiazolidinone 5-[3,5-bis(1,1-dimethylethyl)-4-hydroxyphenylmethyl]-4-thiazolidinone 5-[[3,5-bis(1,1-dimethylethyl)-4-hydroxyphenyl]methyl-2-thioxo-4-thiazolidinone 3-acetyl-5-[3,5-bis(1,1-dimethylethyl)-4-hydroxyphenyl]methylene-4-thiazolidinone 5-[[3,5-bis(1,1-dimethylethyl)-4-hydroxyphenyl]methyl-3-[methyl(1-methylethyl)amino]-4-thiazolidinone 5-[4-hydroxybenzal]rhodanine 5—(4-hydroxy-3-methoxybenzylidene)rhodanine 5-[(4-hydroxy-3,5-dipropylphenyl)methylene]-3-[2—(-dimethylamino)ethyl]-4-thiazolidinone 5-[[3,5-bis(1-methylpropyl)-4-hydroxyphenyl]methyl]-3-methyl-4-thiazolidinone 5-[[3,5-dimethyl-4-hydroxyphenyl]methylene]-3-methyl-4-thiazolidinone 5-[[3,5-bis(1,1-dimethylethyl)-4-hydroxyphenyl]methyl]-3—(methylsulfonyl)-4-thiazolidinone 5-[[4-hydroxy-3,5-bis(1,1-dimethylethyl)phenyl]methyl]-3—(propylamino)-4-thiazolidinone 3-amino-5-[[3,5-bis(1,1-dimethylethyl)-4hydroxyphenyl]methylene]-2-thioxo-4-thiazolidinone 5-[[3,5-bis(1-methylethyl)-4-hydroxyphenyl]methyl]-3-methyl-4-thiazolidinone 5-[(4-hydroxy-3,5-dimethoxyphenyl)methyl]-3-methyl-2-thioxo-4-thiazolidinone 5—(4-hydroxy-3,5-dimethoxyphenyl)methylene]-3-methyl-2-thioxo-4-thiazolidinone Some of the compounds employed in the method of the present invention are known, see, e.g., European Patent Application 211,670 and Teuber et al., *Leibigs Ann. Chem.*, 757 (1978). However, the majority of the compounds used in the method of the present invention, as well as the compounds of the present invention, are novel. In general, these compounds may be synthesized as follows.

Teuber et al. disclose 5-[[3,5-bis(1,1-dimethylethyl)-4-hydroxyphenyl]methylene]-2-thioxo-4-thiazolidinone (referred to in the following discussion as Compound A). The compound is prepared by reacting 3,5-ditert-butyl-4-hydroxybenzaldehyde with rhodanine at reflux temperature in glacial acetic acid using fused sodium acetate as catalyst. 5-[[3,5-Bis(1,1-dimethylethyl)-4-hydroxyphenylmethylene]-4-thiazolidinone (Compound B), 5-[[3,5-bis(1,1-dimethylethyl)-4-hydroxyphenyl]methyl]-4-thiazolidinone (Compound C) and 5-[[3,5-bis(1,1-dimethylethyl)-4-hydroxyphenyl]methyl]-2-thioxo-4-thiazolidinone (Compound D) can be prepared from Compound A.

For example, when Compound A is subjected to catalytic hydrogenation, one obtains both Compounds B and C. The relative proportions obtained depend upon the temperature, pressure, and duration of hydrogenation, the solvent employed, and the particular catalyst used. For example, when Compound A is treated with 5% palladium on carbon in ethanol at 100° C. for approximately 18 hours, the relative ratios of Compound B:C are approximately 60:40. Alternatively, these transformations may be accomplished by heating Compound A in a mixture of hydrochloric acid and an alcohol, such as ethanol, in the presence of zinc. Reduction of the thione without affecting the benzylic double bond may be accomplished by heating the thione with a reducing agent such as tri-n-butyl tin hydride in a nonreactive solvent, such as toluene, and preferably in the presence of a free radical initiator, such as azobisisobutyronitrile. However, for such reduction to work an N-substituted rhodanine substrate (i.e., Q cannot be —NH) must be employed.

The transformation of Compound A to D may be accomplished by a variety of methods known in the art. A preferred method is that taught by Nakamura et al., *Tetrahedron Letters*, 25, 3983 (1984). In this reaction, Compound A is treated with a dihydropyridine such as diethyl 2,6-dimethyl-1,4-dihydro-3,5-pyridinedicarboxylate in the presence of silica gel. The reaction is best carried out in the presence of a nonreactive solvent such as benzene or toluene, preferably under an inert atmosphere. The reaction may be accomplished at temperatures from about 25° C. up to the reflux temperature of the mixture. At the preferred temperature of approximately 80° C., the reaction is essentially complete after 12-18 hours.

Other thiazolidinones may, depending on the values selected for the various substituents, be prepared in an analogous fashion. For example, compounds of Formula I and Formula II wherein Q is $NR^8$ and $R^8$ is hydrogen, $C_1$-$C_6$ alkyl, $C_3$-$C_8$ cycloalkyl or $-(CH_2)_n Y$, where n is an integer from 0 to 3, both inclusive, and Y is cyano or $NR^{11}R^{12}$ where $R^{11}$ and $R^{12}$ are each independently hydrogen or $C_1$-$C_6$ alkyl, may be prepared by the method of Teuber et al. described above, employing the appropriate N-substituted rhodanine and $R^1$, $R^2$-substituted-4-hydroxybenzaldehyde. Alternatively, rhodanine may be used for the condensation with the aldehyde to form those species wherein Q is $NR^8$ and $R^8$ is hydrogen, followed by alkylation with the appropriate $R^8$-containing halide, such as an iodide or bromide, to provide the corresponding N-substituted derivatives; i.e., those compounds of Formulae I or II in which $R^8$ is $C_2$-$C_6$ alkyl, $C_2$-$C_6$ alkenyl, $C_3$-$C_8$ cycloalkyl or $-(CH_2)_n Y$, where Y is cyano, $OR^9$, —SH, —S($C_1$-$C_4$ alkyl), —$NR^{11}R^{12}$ or

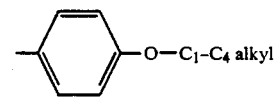

and n, $R^9$, $R^{11}$ and $R^{12}$ are as defined for Formula I. The alkylation is usually accomplished in an inert solvent such as tetrahydrofuran (THF) or dimethylformamide (DMF) in the presence of a strong base such as sodium hydride. In a similar fashion, as is well known in the art, rhodanine may be used for the condensation with the aldehyde forming those species wherein Q is $NR^8$ and $R^8$ is hydrogen followed by substitution with the appropriate $R^8$-containing halide to provide N-substituted derivatives of Formulae I or II in which $R^8$ is $-(CH_2)_n Y$ and Y is

where n and $R^{10}$ are as defined for Formula I.

Compounds of Formulae I and II wherein Q is $NR^8$ and $R^8$ is $-(CH_2)_n Y$ (Y is $OR^9$ or $NR^{11}R^{12}$, wherein $R^9$ is hydrogen,

or tosyl and $R^{11}$ and $R^{12}$ are as defined for Formula I) may also be prepared according to the following reaction scheme:

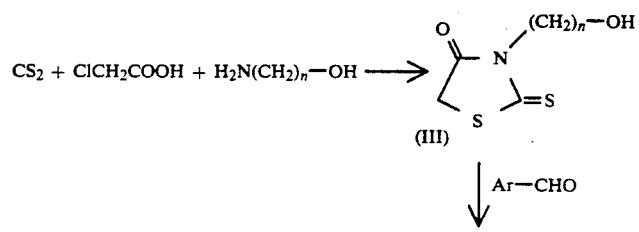

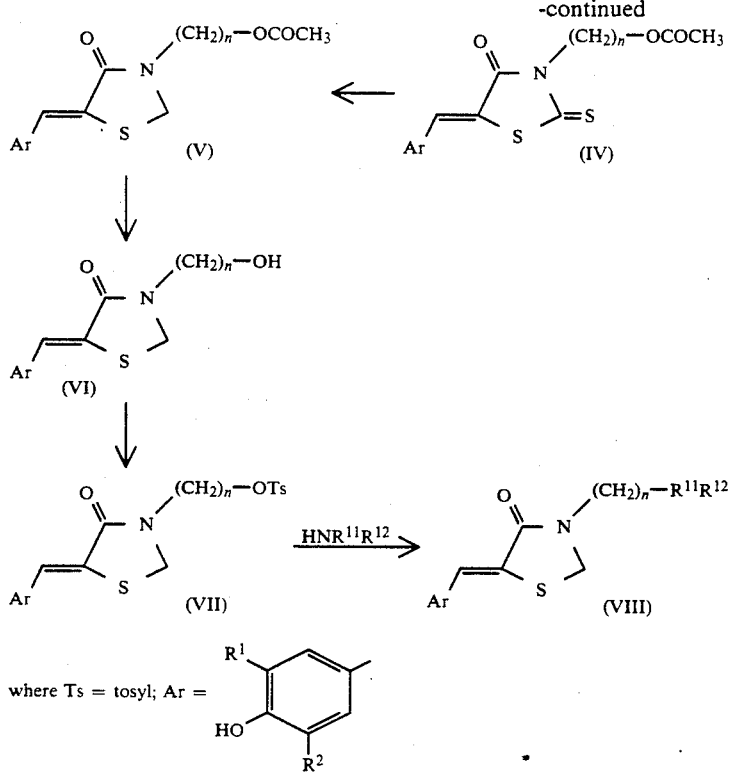

where Ts = tosyl; Ar =

A hydroxyalkyl rhodanine III is prepared by condensing carbon disulfide, chloroacetic acid, and the appropriate hydroxyalkylamine by standard techniques. When condensed with the appropriate $R^1$, $R^2$-substituted-4-hydroxybenzaldehyde, as described above, the resulting product is the condensed 2-thioxo-4-thiazolidinone IV, which has been transformed into the acetyl derivative. The thioxo compound may optionally be converted to the methylene compound of formula V as described above. The acetyl group of intermediate V may be removed upon treatment with aqueous ammonia in a solvent such as acetonitrile to provide compound VI (i.e., the compound of Formulae I and II wherein Q is $NR^8$ and $R^8$ is —$(CH_2)_n$—Y where Y is $OR^9$ and $R^9$ is hydrogen). The hydroxy compound VI is then converted to the tosyl derivative (VII) upon treatment with p-toluenesulfonyl chloride in pyridine, preferably at a temperature of around 0° C. The versatile tosyl intermediate VII may then be transformed into additional compounds of Formulae I and II upon treatment with an appropriate $HNR^{11}R^{12}$ amine, where $R^{11}$ and $R^{12}$ are as stated in the preceeding paragraph. This latter transformation is best accomplished by allowing VII to react in the presence of a molar excess of the amine. Once again, a solvent such as acetonitrile is useful for accomplishing this transformation.

The corresponding 1,3-oxothiolan-5-ones of Formulae I and II may be prepared from β-(3,5-di-t-butyl-4-hydroxyphenyl)-α-mercaptoacrylic acid (IX). Compound IX may be treated with carbon disulfide to prepare the thione analog (Formulae I and II, Q is —O—, $R^6$ and $R^7$ are =S), while reaction of IX with formic acid provides the corresponding desthione (Formulae I and II, Q is —O—, $R^6$ and $R^7$ are each hydrogen). Compound IX can be prepared by known methods (see, e.g., Campaigne et al., *J. Org. Chem.*, 26, 359 (1961); id., 26, 1326 (1961); Chakrabarti, et al., *Tetrahedron*, 25(14), 2781 (1969)), or upon heating Compound A with dilute aqueous base.

Compounds of Formulae I and II wherein Q is $NR^8$ and $R^8$ is —$(CH_2)_n$—Y (n=0) and Y is $NR^{11}R^{12}$, where $R^{11}$ and $R^{12}$ are as defined for Formulae I, may be prepared according to the following reaction sequence:

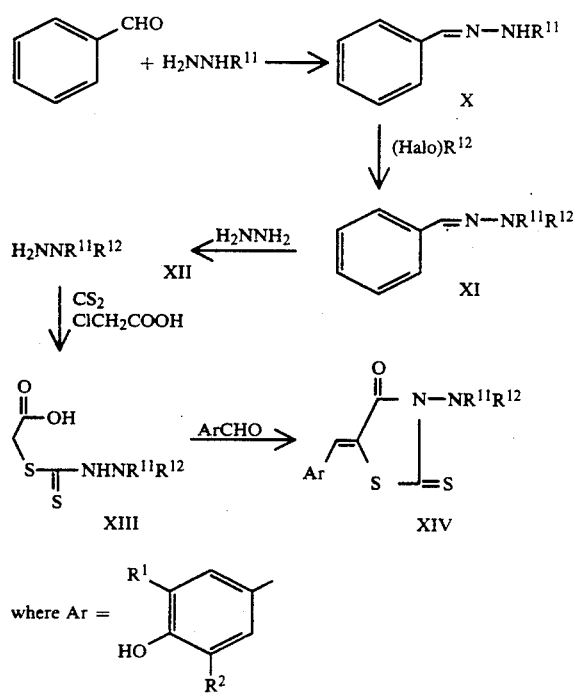

where Ar =

The $R^{11}$-substituted hydrazine is treated with benzaldehyde in an alcoholic (preferably methanol) solvent to yield intermediate X, which, in turn, is reacted with the appropriate $R^{12}$-halide in the presence of triethylamine and acetonitrile to render intermediate XI. XI is then treated with hydrazine to render the $R^{11},R^{12}$-hydrazine, XII. XII may alternatively be prepared by reducing a nitroso-$R^{11}R^{12}$ amine using zinc dust and acetic acid or aluminum and a strong base. The nitroso-$R^{11}R^{12}$ amine itself is prepared from an $R^{11},R^{12}$ amine as described in J. Am. Chem. Soc., 77, 790 (1955) by treatment with sodium nitrite in HCl. XII is then treated with carbon disulfide, chloroacetic acid and triethylamine to yield intermediate XIII. Condensation of XIII with the appropriate $R^1,R^2$-substituted-4-hydroxybenzaldehyde (i.e., ArCHO) renders XIV. As described previously, the thione may be reduced by treatment with a reducing agent such as tri-n-butyl tin hydride in a non-reactive solvent such as toluene, preferably in the presence of a free radical initiator such as azobisisobutyronitrile. Preparation of the species wherein one of $R^{11}$ or $R^{12}$ is hydrogen may be effected before or after reduction of the thione, as desired, by heating the disubstituted compound in a mixture of ethanol/water in the presence of a catalyst, such as a rhodium catalyst.

Those compounds of Formulae I and II wherein X is

and m is 1 or 2 are readily prepared from the sulfide, m=0) by treatment with an oxidizing agent, such as m-chloroperbenzoic acid, in an appropriate organic solvent, such as chloroform, for a time sufficient to effect the desired oxidation.

Compounds of Formulae I and II wherein $R^3$ is $C_1$–$C_6$ alkyl are prepared by conventional Friedel-Crafts alkylation of the appropriate $R^1$, $R^2$-substituted phenol, followed by condensation with rhodanine, or the desired N-substituted rhodanine, as described herein, or is used as described in other reaction schemes depicted herein.

It will be readily appreciated by one skilled in the art that the aryl portion of the present compounds of Formulae I and II are either commercially available or may be readily prepared by known techniques from commercially available starting materials. For example, p-hydroxybenzaldehyde may be alkylated under Friedel-Crafts conditions to yield an alkylbenzaldehyde which in turn may itself be alkylated. Similarly, the rhodanine or N-substituted rhodanine starting material is either commercially available or may be prepared by well known methodology from commercially available starting materials.

Those compounds of Formulae I and II wherein one of $R^6$ or $R^7$ is hydrogen and the other is —OH (and X is

m is 0) are conveniently prepared from their precursors of Formulae I and II where $R^6$ and $R^7$ are both hydrogen (and X is

where m is 1) by treatment of the precursor with, for example, trifluoroacetic anhydride in an inert solvent (preferably methylene chloride) at reduced temperatures. Similarly, compounds of Formulae I and II where, in the definition of Q, Y is cyano are prepared by treating the non-cyanated analog with the desired halo-substituted aliphatic nitrile. From the cyano derivative, the tetrazolyl is prepared by treatment with tri-n-butyl tin azide in, for example, ethylene glycol dimethyl ether. Other compounds of Formulae I and II may be prepared as more fully described below from compounds whose synthesis was described generically, supra.

The method and compounds of the present invention encompass both the racemate and its individual stereoisomers. In general, the stereoisomers may be obtained according to procedures well known in the art. However, for compounds of Formulae I and II wherein X is —S—; $R^4$ and $R^5$ are hydrogen; and $R^1$, $R^2$, $R^3$, $R^6$, $R^7$ and Q are as defined for those Formulae, the individual stereoisomers may be isolated in substantially pure isomeric form according to the following novel process. In the following process, preferred compounds whose stereoisomers may be isolated are those compounds of Formulae I or II wherein X is —S—; $R^4$ and $R^5$ are hydrogen; and $R^1$, $R^2$, $R^3$, $R^6$, $R^7$ and Q are as defined for the preferred, somewhat preferred, particularly preferred, especially preferred and most preferred compounds of the method of the present invention, discussed above.

The racemic sulfide compound of Formulae I or II is reacted with a reagent prepared by combining a tartrate ligand, a titanium alkoxide, a hydroperoxide and, optionally, water. Suitable titanium alkoxides for use in the present process include titanium alkoxides having the formula $Ti(C_1–C_4 \text{ alkoxy})_4$. A particularly preferred titanium alkoxide is one wherein the $C_1$–$C_4$ alkoxy group is isopropoxy. Similarly, suitable tartrate ligands for use in the present process include the di($C_1$–$C_4$ alkyl) tartrates, with diethyl tartrate or diisopropyl tartrate particularly preferred. Finally, suitable hydroperoxides which may be used in the present process include cumenehydroperoxide, t-butylhydroperoxide, and the like. A particularly preferred hydroperoxide is t-butylhydroperoxide.

The present reaction is conducted by mixing the above reagents in an inert solvent. Suitable inert solvents include aromatic solvents such as toluene and the like; halogenated alkanes such as methylene chloride, 1,2-dichloroethane, chloroform and the like; ethers such as tetrahydrofuran, diethyl ether and the like; and ketones such as acetone and the like. A particularly preferred inert solvent is methylene chloride. In general, the amount of solvent used should be sufficient to ensure that all compounds stay in solution during reaction. However, excessive amounts of solvent should be avoided since unnecessary product loss may occur during product isolation.

The amount of titanium alkoxide used in the present reaction is not critical. The titanium alkoxide may be employed in quantities of from about 0.4 equivalents to about 2.0 equivalents relative to the racemic sulfide starting material. For reasons explained more fully below, the titanium alkoxide is preferably employed in quantities sufficient to provide a titanium alkoxide/sulfide substrate ratio of from about 0.5/1.0 to about 0.75/1.0. If the titanium alkoxide is used in less than equimolar quantities relative to the sulfide starting material, 3Å— or 4Å— molecular sieves may be added, if desired, to avoid the possibility of water deactivation of the titanium complex.

The amount of tartrate ligand, hydroperoxide and water employed are based on the amount of titanium alkoxide used, and are also not critical. In general, the tartrate ligand is employed in quantities sufficient to provide a tartrate ligand/titanium alkoxide ratio of from about 1/1 to about 5/1, with a preferred ratio being about 2/1. Similarly, the hydroperoxide may be employed in from about equimolar quantities relative to the titanium alkoxide to about two equivalents relative to that same compound. The amount of water employed may vary from anhydrous reaction condition (i.e. no equivalents of water) to as much as about 5 equivalents of water relative to the amount of titanium alkoxide present. When anhydrous reaction condition are employed, the tartrate ligand should be used in an amount sufficient to provide a tartrate ligand/titanium alkoxide ratio corresponding to the higher end of the tartrate ligand/titanium alkoxide ratio described above.

The stereochemistry of the tartrate ligand determines which stereoisomer will be obtained from the racemic sulfide substrate. For example, if (+)diisopropyltartrate is employed in the present reaction the (−) enantiomer of the sulfide starting material will be isolated in substantially pure isomeric form. Correspondingly, if (−)-diethyltartrate is used, substantially pure (+) enantiomer of the sulfide substrate will be obtained. Accordingly, the tartrate ligand must be chosen so that its stereochemistry is opposite that of the isomeric form desired.

The racemic sulfide substrate of the present process is reacted with the reagent prepared from the titanium alkoxide, the tartrate ligand, the hydroperoxide and, optionally, water until substantially all of the undesired enantiomer of the sulfide starting material has been converted to its sulfoxide analog. Conversion to the sulfoxide readily occurs at temperatures in the range of from about −50° C. to about 50° C., with a preferred temperature being about −20° C. Once substantially all of the undesired enantiomer has been converted to its sulfoxide analog, the reaction is terminated by quenching the reaction mixture according to techniques well known in the art.

To ensure that substantially all of the undesired enantiomer is converted to the sulfoxide, while minimizing conversion of the desired enantiomer, only about 50 to about 70 percent of the racemic sulfide substrate should be allowed to react with the reagent containing titanium alkoxide. Limiting reaction to between about 50% to about 70% may be accomplished in at least two ways. Firstly, the hydroperoxide may be employed in quantities which provide a hydroperoxide/sulfide substrate ratio of from about 0.5/1.0 to about 0.75/1.0. Alternatively, the hydroperoxide may be used in amounts greater than about 0.75 equivalents relative to the sulfide substrate provided the progress of the reaction is monitored by standard analytical techniques such as thin layer chromatography (TLC) or high performance liquid chromatography (HPLC). Once these techniques indicate that between about 50 to about 70 percent of the sulfide starting material has been converted the reaction is quenched to prevent further conversion.

Once the reaction has been quenched the unreacted portion of the sulfide substrate may be recovered from the quenched reaction mixture using techniques well known to those skilled in the art. This unreacted portion will consist of the desired enantiomer in substantially pure enantiomeric form.

The following examples further illustrate the preparation of the compounds of this invention, as well as the compounds used in the method of this invention. The examples also illustrate the process for selective enantiomeric isolation provided by the present invention. The examples are illustrative only and are not intended to limit the scope of the invention in any way.

EXAMPLE 1

5-[[3,5-Bis(1,1-dimethylethyl)-4-hydroxyphenyl]methylene]-2-thioxo-4-thiazolidinone (Compound A)

Under a nitrogen atmosphere, 117.2 g of 3,5-di-tert-butyl-4-hydrox-ybenzaldehyde, 66.6 g of rhodanine, and 143.5 g of fused sodium acetate were heated at reflux in 2500 ml of glacial acetic acid. After heating for 23 hours, the reaction mixture was cooled and poured into a mixture of 1 liter of ethanol and 1 liter of ice, with stirring. Water (500 ml) was added and, after stirring for 30 minutes, the resulting precipitate was recovered by filtration. The solid was slurried with 500 ml of ethyl acetate and filtered. The precipitate was dissolved in 3 liters of ethanol, heated to boiling, and water was added until the solution remained cloudy (approximately 450 ml of water). Upon cooling to room temperature, 99.6 g of title product were recovered by filtration, m.p. approximately 260° C.

Analysis for $C_{18}H_{23}NO_2S_2$:
Calculated: C, 61.86; H, 6.63; N, 4.01.
Found: C, 62.13; H, 6.55; N, 4.15.

EXAMPLES 2-3

5-[[3,5-Bis(1,1-dimethylethyl)-4-hydroxyphenyl]methylene]-4-thiazolidinone (Compound B) and 5-[[3,5-Bis(1,1-dimethylethyl)-4-hydroxyphenyl]methyl4-thiazolidinone (Compound C)

A solution of 69.90 g of 5-[[3,5-bis(1,1-dimethylethyl)-4-hydroxyphenyl]methylene]-2-thioxo-4-thiazolidinone in 4 liters of ethanol was hydrogenated at 500 pounds per square inch in the presence of 200 g of 5% palladium on carbon overnight at 100° C. The reaction mixture was filtered and evaporated to dryness. In sections, the material was dissolved in 1 volume of hot ethyl acetate, diluted with 2 volumes of hexane, filtered, and loaded onto a silica gel chromatography column. Elution with 35% ethyl acetate in hexane provided various fractions which were combined according to the purities of the respective compounds. A total of 4.6 g of Compound B were isolated by chromatography. Fractions which were predominantly Compound B were crystallized from ethyl acetate/hexane providing a total yield of Compound B of 13.79 g. Rechromatography of fractions containing impure Compound C on silica eluting with 25% ethyl acetate in hexane provided 9.82 g of Compound C.

2. 5-[[3,5-bis(1,1-dimethylethyl)-4-hydroxy phenyl]methylene]-4-thiazolidinone, m.p. 209°–213° C.

Analysis for $C_{18}H_{25}NO_2S$:
Calculated: C, 67.67; H. 7.89; N, 4.38.

Found: C 67.44: H, 8.11: N, 4.65.
3. 5-[3,5-bis(1,1-dimethylethyl)-4-hydroxyphenylmethyl]-4-thiazolidinone, m.p. 149°–152° C.
Analysis for $C_{18}H_{27}NO_2S$:
Calculated: C, 67.25; H, 8.47; N, 4.36.
Found: C, 67.43; H, 8.44; N, 4.21.

EXAMPLE 4

5-[[3,5-Bis(1,1-dimethylethyl)-4-hydroxyphenyl]methyl]-2-thioxo-4-thiazolidinone (Compound D)

Under a nitrogen atmosphere, 13.98 g of 5-[3,5-bis(1,1-dimethylethyl)-4-hydroxyphenyl]methylene-2-thioxo-4-thiazolidinone, 13.17 g of die 2,6-dimethyl-1,4-dihydro-3,5-pyridinedicarboxylate and 600 ml of toluene were stirred to effect solution. Forty grams of silica gel 60 (finer than 230 mesh), previously dried in vacuo at 50° C. for 7 hours, were added to the reaction. The reaction was heated at reflux for 18 hours and filtered hot. The filtrate was evaporated to dryness. The residue was dissolved in 500 ml of ethyl acetate, washed 5 times each with 400 ml of 1N hydrochloric acid, dried over sodium sulfate, filtered, and evaporated in vacuo to provide a yellow solid. Chromatography over silica gel eluting with 2.5% ethyl acetate in toluene provided 8.0 g of title product, m.p 178°–179° C.
Analysis for $C_{18}H_{25}NO_2S_2$:
Calculated: C, 61.50; H, 7.17; N, 3.98.
Found: C, 61.28; H, 7.19; N, 3.94.

EXAMPLE 5

5-[3,5-Bis(1,1-dimethylethyl)-4-hydroxyphenyl]methylene]-3-methyl-2-thioxo-4-thiazolidinone The title compound was prepared in 76% yield from 3,5-di-tert-butyl-4-hydroxybenzaldehyde and N-methylrhodanine following the procedure of Example 1, m.p. >230° C.
Analysis for $C_{19}H_{25}NO_2S_2$:
Calculated: C, 62.77; H, 6.93; N, 3.85; S, 17.64.
Found: C, 62.54; H, 7.05; N, 3.66; S, 17.82.

EXAMPLE 6

5-[[3,5-Bis(1,1-dimethylethyl)-4-hydroxyphenyl]methylene]-3-methyl-4-thiazolidinone The title compound was prepared in 71% yield from 10.31 g of the thione of Example 5 upon heating with 38.15 ml of tri-n-butyltin hydride and 1.16 g of azobisisobutyronitrile (AIBN) in 142 ml of toluene at reflux temperature for one hour. The product was isolated by adding water to the cooled reaction mixture, separating the layers, washing the organic layer with 1N hydrochloric acid and a saturated sodium chloride solution, drying over magnesium sulfate, concentrating in vacuo, and purifying the residue by chromatography over silica gel eluting with a 10–50% hexane in ethyl acetate gradient. The purified product had a melting point of 142°–144° C.
Analysis for $C_{19}H_{27}NO_2S$:
Calculated: C, 68.43; H, 8.16; N, 4.20.
Found: C, 68.68; H, 8.00; N, 3.97.

EXAMPLE 7

5-[[3,5-Bis(1,1-dimethylethyl)-4-hydroxyphenyl]methyl]-3-methyl-4-thiazolidinone To 100 ml of THF were added 6.43 g of the compound of Example 3. Sodium hydride (0.9 g) was added, resulting in the evolution of a gas. Iodomethane (1.25 ml, 1.0 eq.) was added and the resultant mixture was stirred at room temperature for 23 hours after which the mixture was diluted with a volume of diethyl ether and 1N HCl. The organic layer was separated and dried over sodium sulfate, filtered and evaporated. The resultant solid was chased with chloroform to render an orange foam. A 5.93 g sample of this material was dissolved in 14 ml of a hot mixture of ethyl acetate diluted with 225 ml of hexane and then allowed to cool to room temperature overnight. The solvent was evaporated and the resultant solid was dissolved in 40 ml of a hot mixture of diethyl ether diluted with about 400 ml of hexane. The mixture was allowed to cool to room temperature overnight and a precipitate formed which was collected by filtration, washed with hexane and dried in vacuo to render 3.98 g of title compound, m.p. 102°–105° C.
Analysis for $C_{19}H_{29}NO_2S$:
Calculated: C, 68.02; H, 8.71; N, 4.17.
Found: C, 68.22; H, 8.80; N, 4.21.

EXAMPLE 8

5-[[3,5-Bis(1,1-dimethylethyl)-4-hydroxyphenyl]methylene]-3-dimethylamino-2-thioxo-4-thiazolidinone The title compound was prepared in 65% yield from 3,5-di-tert-butyl-4-hydroxybenzaldehyde and N-dimethylaminorhodanine following the procedure of Example 1.

EXAMPLE 9

5-[[3,5-Bis(1,1-dimethylethyl)-4-hydroxyphenyl]methylene]-3-dimethylamino-4-thiazolidinone The compound of Example 8 was reduced using the procedure of Example 6 to provide the title compound in 41% yield, m.p. 138°–141° C.
Analysis for $C_{20}H_{30}N_2O_2S$:
Calculated: C, 66.26; H, 8.34; N, 7.73.
Found: C, 66.55; H, 8.59; N, 7.47.

EXAMPLE 10

5-[[3,5-Bis(1,1-dimethylethyl)-4-hydroxyphenylmethylene]-3—(methylamino)-4-thiazolidinone A. Preparation of benzaldehydemethylhydrazone
Benzaldehyde (50.8 ml, 500 mmol) and 26.5 ml (500 mmol) of methylhydrazine were dissolved in 1 liter of methanol. The mixture was stirred together at room temperature for 75 minutes and then stripped of solvent to give 67.8 g of the subtitled intermediate.
B. Preparation of benzaldehyde N-methyl, N-2-propenylhydrazone
The above compound (67.8 g), 60.5 g of allyl bromide and 50.5 g of triethylamine were dissolved together in 1 liter of acetonitrile. The mixture was heated at reflux temperature for 16 hours and then cooled. An additional 45 g of allyl bromide and 38 g of triethylamine were added and the mixture was again heated at reflux for an additional 7 hours, cooled and then stripped of solvent to yield 268 g of a residue. To this residue was added 500 ml of THF and the resultant mixture was shaken, filtered and washed with an additional 125 ml of THF. The filtrate was stripped of solvent to yield 67 g of the subtitled intermediate.
C. Preparation of N-methyl, N-2-propenylhydrazine
The above compound (59.9 g), 44 g of hydrazine and 137 ml of ethanol were heated at reflux temperature for 21.5 hours and allowed to cool. The reflux condenser was replaced with a distillation head and the mixture was distilled at one atmosphere pressure. The first three distillates were collected, combined and 100 ml of 1N HCl were added. An additional 100 ml of concentrated HCl were added, with ice, and the resultant mixture separated and washed with a small amount of ethyl acetate. The resultant layers were separated and the water distilled off until solids clogged the stir bar. The solids were filtered off and the filtrate was stripped and added to 125 ml of chilled 50% NaOH. The resulting solid was filtered off and discarded. The filtrate contained two layers which were separated. The top layer contained the subtitled intermediate and the bottom, aqueous layer, was extracted with diethyl ether which, upon stripping, gave additional product.

D. Preparation of N-Methyl, N-3-propenyl-5-carboxymethyl-dithiocarbamate

To 12.67 g of the above compound in 23 ml of ethanol chilled to 0° C. was added a solution of 11.18 g of carbon disulfide in 26 ml of diethyl ether. The resultant mixture was removed from the ice bath and allowed to stand at room temperature for about 15.5 hours, after which the solvent was stripped to yield approximately 36.5 g of a residue. To this residue was added 13.9 g of chloroacetic acid dissolved in 29.5 ml of 5N NaOH (chilled in an ice bath). The resultant solution was allowed to stand for 3 hours at room temperature. The pH of the solution was lowered to about 3 by adding 8 ml of concentrated hydrochloric acid. Diethyl ether (50 ml) was then added, resulting in a three phase separation. The aqueous phases were pooled and extracted with 50 ml of chloroform, then stripped of solvent to yield approximately 40.4 g of the subtitled intermediate.

E. Preparation of 5-[[3,5-bis(1,1-dimethylethyl)-4-hydroxyphenyl]methylene]-2-thioxo-3-(methyl-2-propenylamino)-4-thiazolidinone 3,5-Di-tert-butyl-4-hydroxybenzaldehyde (29.3 g), 38.8 g of the above compound and 40.34 g of sodium acetate were mixed in 810 ml of acetic acid and the resultant solution heated at reflux temperature for 24 hours. The solution was allowed to cool and stirred for an additional 60 hours at room temperature. The solution was then poured into 2 liters of ice water, separated and washed with an additional volume of water to yield about 44 g of the subtitled intermediate.

F. Preparation of 5-[[3,5-bis(1,1-dimethylethyl)-4-hydroxyphenyl]methylene]-3—(methyl-2-propenylamino)-4-thiazolidinone Utilizing the procedure described in Example 6, 42.8 g of the above thione were reduced to the subtitled intermediate (8.34 g).

G. Preparation of 5-[[3,5-bis(1,1-dimethylethyl)-4-hydroxyphenylmethylene]-3—(methylamino)-4-thiazolidinone The above compound (6.11 g) was dissolved in a mixture of 135 ml ethanol and 15.3 ml of water and the mixture was heated to 70° C. Tris-(triphenylphosphine)rhodium (I) chloride (50 mg) was added and the mixture heated at reflux temperature for 50 minutes, after which an additional 550 mg of the catalyst were added followed by heating at reflux temperature for an additional 2.5 hours. The mixture was cooled and stirred at room temperature overnight and stripped of solvent to give 2.05 g of title product after further workup, m.p. 151°-153.5° C.

Analysis for $C_{19}H_{28}N_2O_2S$:
Calculated: C, 65.86; H, 7.56; N, 8.09.
Found: C, 65.67; H, 7.81; N, 8.34.

EXAMPLES 11 and 12

5-[(3,5-Di-2-propenyl-4-hydroxyphenyl)methylene]-4-thiazolidinone and
5—(3,5-Di-2-propenyl-4-hydroxyphenyl)methyl-4-thiazolidinone A. Preparation of 3,5-di-(2-propenyl)-4-hydroxybenzaldehyde Under a nitrogen atmosphere and using a mechanical stirrer, 250 g of parahydroxybenzaldehyde, 247.6 g of allyl bromide, 311.7 g of potassium bicarbonate and 650 ml of acetone were heated to reflux temperature for about 18 hours. The mixture was allowed to cool, after which about 1 liter of water was added followed by extraction with two 800 ml portions of diethyl ether. Subsequent distillation of the organic phase rendered about 299 g of 4-(2-propenyl)oxybenzaldehyde which was then heated with about 300 ml of diethylaniline for 5.5 hours at 195°-205° C. The mixture was cooled and 750 ml of ethyl acetate were added. The mixture was washed with three 500 ml portions of 1N HCl which, followed by subsequent workup, yielded about 138 g of 3—(2-propenyl)-4-hydroxybenzaldehyde. The monosubstituted aldehyde (159 g) was again heated to reflux with 152 g of potassium carbonate and 465 ml of acetone for 3 hours and then allowed to cool. The mixture was poured into 900 ml of ice water and subsequently extracted with two 430 ml portions of diethyl ether to yield about 170 g of 3—(2-propenyl)-4—(2-propenyloxy)benzaldehyde. The di-substituted aldehyde was then heated, in about 500 ml of diethylaniline, under a nitrogen atmosphere to 195°-205° C. for about 6.5 hours. The mixture was cooled and dissolved in about 800 ml of ethyl acetate, washed with three 1 liter portions of 1N HCl and, following workup, rendered about 121.9 g of the subtitled intermediate.

B. Preparation of 5-[(3,5-di-2-propenyl-4-hydroxyphenyl)methylene]-2-thioxo-4-thiazolidinone The above compound (50.5 g), 36.6 g of rhodanine and 164 g of sodium acetate were heated together at reflux temperature in 1.25 liters of acetic acid for 14.5 hours. The resultant solution was cooled, poured into 2 liters of ice water to yield, upon separation, about 75 g of the subtitled intermediate, m.p. 157°-160° C.

C. Preparation of 5-[(3,5-di-2-propenyl-4-hydroxyphenyl]methylene]-4-thiazolidinone and 5-[(3,5-di-2-propenyl-4-hydroxyphenyl)methyl]-4-thiazolidinone The above compound (74.8 g) was reduced by treatment with zinc dust (62 g) and concentrated hydrochloric acid (950 ml) in 2.1 liters of hot (approximately 82° C.) ethanol. Once the reactants were combined the solution was allowed to cool to room temperature, stirred for one hour, and then added to 3.75 liters of ice water. The resulting solution was allowed to sit overnight to provide a gum. The liquid layer was decanted and extracted with 750 ml of chloroform, while the gum was dissolved in 560 ml of chloroform and the resulting solution washed, successively, with 75 ml of a saturated sodium carbonate solution, 75 ml of water and 75 ml of a saturated brine solution. The above chloroform solutions were combined and then triturated with 100 ml of methylene chloride. The titled products were obtained using silica gel chromatography. Elution with a 25-60% ethyl acetate in hexane gradient provided various fractions which were treated as follows.

Fractions 13-15 were concentrated and then washed with ethyl acetate to provide 2.91 g of 5-[(3,5-di-2- propenyl-4-hydroxyphenyl)methyl]-4-thiazolidinone. Fractions 16-18 were concentrated to a residue which was triturated with 30 ml of methylene chloride. Fractions 19-23 were concentrated to a residue which was triturated with 35 ml of methylene chloride. Following trituration, the remaining insolubles were isolated by filtration and triturated with 40 ml of ethyl acetate to provide 3.85 g of 5-[(3,5-di-2-propenyl-4-hydroxyphenyl)methylene]-4-thiazolidinone.

The ethyl acetate wash from fractions 13-15, the methylene chloride solution containing fractions 16-18 and the methylene chloride and ethyl acetate solutions obtained from fractions 19-23 were combined and loaded onto a silica gel chromatography column. Elution with a 1:1 ethyl acetate/hexane solution provided various fractions which were combined according to the purities of the respective compounds. Fractions which were predominately 5-[(3,5-di-2-propenyl-4-hydroxyphenyl)methyl]-4-thiazolidinone were crystallized from hot ethyl acetate to provide 1.24 g of that compound (total yield of 5-[(3,5-di-2-propenyl-4-hydroxyphenyl)methyl]-4-thiazolidinone - 4.14 g). Fractions which were predominately 5-[(3,5-di-2-propenyl-4-hydroxyphenyl)methylene]-4-thiazolidinone were triturated with 30 ml of hot ethyl acetate to provide 1.73 g of that compound (total yield of 5-[(3,5-di-2-propenyl-4-hydroxyphenyl)methylene]-4-thiazolidinone - 5.58 g).

11. 5-[(3,5-di-2-propenyl-4-hydroxyphenyl)methylene]-4-thiazolidinone, m.p. 184°-188° C.
Analysis for $C_{16}H_{17}NO_2S$:
Calculated: C, 66.87; H, 5.96; N, 4.87.
Found: C, 66.62, H, 5.92; N, 4.89.

12. 5-[3,5-di-2-propenyl-4-hydroxyphenyl)methyl]-4-thiazolidinone, m.p. 142°-144° C.
Analysis for $C_{16}H_{19}NO_2S$:
Calculated: C, 66.41; H, 6.62; N, 4.84.
Found: C, 66.18; H, 6.69; N, 4.60.

Utilizing the procedures set forth in Examples 11, 12, and elsewhere herein, the following additional compounds were prepared.

EXAMPLE 13

5-[(3,5-Di-2-propenyl-4-hydroxyphenyl)methylene]-3-methyl-4-thiazolidinone, m.p. 155°-159° C.

Analysis for $C_{17}H_{19}NO_2S$:
Calculated: C, 67.74; H, 6.35; N, 4.65.
Found: C, 67.53; H, 6.09; N, 4.45.

EXAMPLE 14

5-[(3,5-Dipropyl-4-hydroxyphenyl)methylene]-3-methyl-4-thiazolidinone, m.p. 162°-165° C.

Analysis for $C_{17}H_{23}NO_2S$:
Calculated: C, 66.85; H, 7.59; N, 4.59.
Found: C, 67.12; H, 7.37; N, 4.52.

EXAMPLE 15

5-[(3,5-Dipropyl-4-hydroxyphenyl)methylene]-4-thiazolidinone, m.p. 202°-205° C.
Analysis for $C_{16}H_{21}NO_2S$:
Calculated: C, 65.95; H, 7.26; N, 4.81.
Found: C, 66.16; H, 7.49; N, 4.79.

EXAMPLE 16

5-[(3,5-Dipropyl-4-hydroxyphenyl)methyl]-4-thiazolidinone, m.p. 155°-157° C.

Analysis for $C_{16}H_{23}NO_2S$:
Calculated: C, 65.49; H, 7.90; N, 4.77.
Found: C, 65.71; H, 7.73; N, 4.99.

EXAMPLE 17

5-[[3-(1,1-Dimethylethyl)-4-hydroxy-5-methylphenyl]methylene-4-thiazolidinone.

A. Preparation of 4-hydroxy-3-methyl-5-(1,1-dimethylethyl)benzaldehyde

Under a nitrogen atmosphere, 76.65 g of 2-(1,1-dimethylethyl)-6-methylphenol (Aldrich), 65.42 g of hexamethylenetetramine and 700 ml of trifluoroacetic acid were stirred at reflux temperature for about 24 hours. The reaction solution was allowed to cool and the liquid removed by evaporation. The resulting residue was taken up in 1500 ml of water and 1000 ml of chloroform and then neutralized to pH 7 with solid sodium carbonate. The resultant layers were separated and the aqueous layer was washed with chloroform. The organic layer was combined with the chloroform wash and the resulting solution was washed with water, then dried over sodium sulfate overnight. After removal of the sodium sulfate the chloroform was evaporated. The resultant residue was taken up in 375 ml of toluene, heated on a steam bath and then allowed to cool to room temperature overnight. Subsequent workup gave 28.3 g of the subtitled intermediate.

B. Preparation of 5-[[3-(1,1-dimethylethyl)-4-hydroxy-5-methylphenyl]methylene]-2-thioxo-4-thiazolidinone The above intermediate (28.3 g), 24 g of N-aminorhodanine, 48.3 g of sodium acetate in 735 ml of acetic acid were heated to reflux temperature for about 7 hours and then allowed to cool to room temperature with continual stirring overnight. The resultant mixture was poured into 1500 ml of ice water with stirring and then filtered. The wet filter cake was transferred to a beaker and dissolved in a mixture of ethyl acetate and water. The resulting organic and aqueous layers were separated. The organic layer was dried over sodium sulfate and then filtered to remove that substance. Further workup, followed by trituration in hot chloroform and subsequent drying under vacuum, rendered about 18 g of the subtitled intermediate, m.p. 210°-216° C.

C. Preparation of 5-[[3-(1,1-dimethylethyl)-hydroxy-5-methylphenyl]methylene]-4-thiazolidinone.

Reduction of the above thione was effected by methods described herein which, following workup, rendered 1.56 g of the titled product, m.p. 162°-165° C.

Analysis for $C_{15}H_{19}NO_2S$:
Calculated: C, 64.95; H, 6.90; N, 5.05.
Found: C, 65.12; H, 7.05; N, 4.99.

Utilizing the procedures set forth in Example 17, and elsewhere herein, the following additional compounds were prepared.

EXAMPLE 18

5-[[3,5-Bis(1-methylethyl)-4-hydroxyphenylmethylene]-3-methyl-4-thiazolidinone, m.p. 200°-210° C.

Analysis for $C_{17}H_{23}NO_2S$:
Calculated: C, 66.85; H, 7.59; N, 4.59.
Found: C, 67.03; H, 7.55; N, 4.37.

EXAMPLE 19

5-[[3,5-Bis(1-methylethyl)-4-hydroxyphenyl]methyl]-2-thioxo-4-thiazolidinone

EXAMPLE 20

5-[[3-(1,1-Dimethylethyl)-4-hydroxy-5-methylphenyl]-methyl]-4-thiazolidinone

A solution of 0.28 g of the compound of Example 17 in 30 ml of tetrahydrofuran was hydrogenated at 60 pounds per square inch in the presence of 1.12 g of 5% palladium on carbon overnight at 60° C. The reaction mixture was filtered and evaporated to dryness. The resulting residue was dissolved in 3.5 ml of a 1:1.5 ethyl acetate/hexane solution and loaded onto a silica gel chromatography column. Elution with 40% ethyl acetate in hexane produced fractions which, upon evaporation to dryness, provided 0.05 g of title compound. m.p. 64°–68° C.

Analysis for $C_{15}H_{21}NO_2S$:
Calculated: C, 64.48; H, 7.58; N, 5.01.
Found: C, 64.32; H, 7.66; N, 4.79.

EXAMPLE 21

5-[[3,5-Bis(1-methylethyl)-4-hydroxyphenyl]methyl]-4-thiazolidinone

Using the method described in Example 20, 4.73 g of the compound of Example 19 were converted to 1.88 g of title compound. m.p. 136°–139° C.

Analysis for $C_{16}H_{23}NO_2S$:
Calculated: C, 65.49; H, 7.90; N, 4.77.
Found: C, 65.79; H, 7.90; N, 4.81.

EXAMPLE 22

5-[[3-(1,1-Dimethylethyl)-4-hydroxy-5-propylphenyl]-methyl]-4-thiazolidinone

A. Preparation of 3-[2-(1,1-dimethylethyl)phenoxypropene

Allyl bromide (69.2 ml), 2-t-butylphenol (122.9 ml) and potassium carbonate (121.6 g) were stirred in 265 ml of acetone at reflux temperature for 50 hours and then cooled to 35° C. Water (600 ml) was added and the resulting layers were separated. The aqueous layer was extracted with 600 ml of diethyl ether. The organic layer was combined with the aqueous layer's ether extract and the resulting solution was dried over sodium sulfate overnight. After sodium sulfate removal, the solvent was evaporated to provide, after further workup, 147 g of the subtitled intermediate.

B. Preparation of 2-(1,1-dimethylethyl)-6-(2-propenyl)-phenol

All 147 g of the above compound were rearranged as described in Examples 11A and 12A to provide 100.8 g of the subtitled intermediate.

C. Preparation of 2-(1,1-dimethylethyl)-6propylphenol.

A solution of 54.9 g of the above compound in ml of toluene was hydrogenated at 60 pounds per square inch in the presence of 55 g of Raney nickel for hours at room temperature. The reaction mixture was filtered and evaporated to dryness to provide 59.2 g of the subtitled intermediate.

D. Preparation of 3-(1,1-dimethylethyl)-4-hydroxy-5-propylbenzaldehyde.

The above compound (55.48 g) was converted to 23.33 g of the subtitled intermediate using the method described in Example 17A.

E. Preparation of 5-[[3-(1,1-dimethylethyl)-hydroxy-5-propylphenyl]methylene]-2-thioxo-4-thiazolidinone.

Using the method described in Example 17B, 5.51 g of the above compound were converted to 6.26 g of the subtitled intermediate m.p. 190.5°–192° C.

F. Preparation of 5-[[3-(1,1-dimethylethyl-4-hydroxy-5-propylphenyl]methyl]-2-thioxo-4-thiazolidinone.

Using the method described in Example 4, 4.73 g of the above compound were converted to 2.1 g of the subtitled intermediate.

G. Preparation of 5-[[3-(1,1-dimethylethyl-4-hydroxy-5-propylphenyl]methyl]-4-thiazolidinone.

A solution of 2.1 g of the above compound in 185 ml of ethanol was hydrogenated at 500 pounds per square inch in the presence of 8.4 g of 5% palladium on carbon for 20 hours at 100° C. The reaction mixture was filtered and evaporated to dryness. The resulting residue was dissolved in 25 ml of methylene chloride and loaded onto a silica gel chromatography column. Elution with 2000 ml of a 10–50% ethyl acetate in hexane gradient, followed by elution with 2000 ml of a 1:1 ethyl acetate/hexane solution, provided fractions which, upon evaporation to dryness, rendered 0.75 g of titled product. m.p. 50°–55° C.

Analysis for $C_{17}H_{25}NO_2S$:
Calculated: C, 66.41; H, 8.20: N, 4.56.
Found: C, 66.61; H, 8.22; N, 4.55.

EXAMPLE 23

5-[[3-Methylthiophenyl-4-hydroxy-5-ethoxyphenyl]methylene]-3-dimethylamino-4-thiazolidinone.

A. Preparation of 5-[[3-ethoxy-4-hydroxyphenyl]methylene]-3-dimethylamino-2-thioxo-4-thiazolidinone.

3-Ethoxy-4-hydroxybenzaldehyde (45.7 g), N-dimethylaminorhodanine (53.35 g) and fused sodium acetate (92.4 g) were reacted in the manner described in Example 1 to provide 52.92 g of the subtitled intermediate. m.p. 194°–198° C.

B. Preparation of 5-[[3-ethoxy-4-hydroxyphenyl]methylene]-3-dimethylamino-4-thiazolidinone.

Using the method described in Example 6, 47.66 g of the above compound were converted to 14.02 g of the subtitled intermediate.

C. Preparation of 5-[3-ethoxy-4-hydroxy-(methylthiophenyl)phenyl]methylene-3-dimethylaminothiazolidinone.

Sodium hydroxide (0.95 g) and 17.3 ml of a 40% by weight solution of formaldehyde were dissolved in 50 ml of 2-ethoxyethanol. Phenylthiol (2.62 g) and 7.0 g of the above compound were added and the resulting solution was refluxed for 4 hours, then cooled. Ethyl acetate (50 ml) and water (25 ml) were added to the cooled reaction mixture and the pH of the resulting two-phase solution was lowered to approximately 5 using concentrated hydrochloric acid. The organic phase was separated from the aqueous phase, washed with a saturated brine solution and then loaded onto a silica gel chromatography column. Elution with 4 liters of methylene chloride, followed by 4 liters of a 3% methanol/97% methylene chloride solution, provided fractions containing the title product. These fractions were combined and loaded once more onto a silica gel chromatography column. Elution with 4 liters of methylene chloride, followed by 1 liter of a 22.5% acetonitrile in methylene chloride solution, provided fractions which, upon evaporation of the solvent, rendered title product. This product was further purified by trituration with a hot solution of 50. ml of hexane and 30 ml of ethyl acetate to provide 6.20 g of 5-[[3-methylthiophenyl-4-hydroxy-5-ethoxyphenylmethylene-3-dimethylamino-4-thiazolidinone. m.p. 118°–120° C.

Analysis for $C_{21}H_{24}N_2O_2S_2$:
Calculated: C, 60.55; H, 5.81; N, 6.73; S, 15.39.
Found: C, 60.75; H, 5.76; N, 6.76; S, 15.58.

EXAMPLE 24

(−)-5-[[3,5-Bis(1,1-dimethylethyl)-4-hydroxyphenylmethyl]-4-thiazolidinone.

To a 50 ml, three-neck, round bottom flask containing 25 ml of methylene chloride were added 1.31 g of 4Å — molecular sieves, 0.56 ml (1.88 mmol) of titanium isopropoxide, 0.79 ml (3.75 mmol) of (+)-diisopropyl resulting solution was stirred for twenty minutes and then 0.8 g (2.5 mmol) of a racemic mixture of 5-[[3,5-bis(1,1-dimethylethyl)-4-hydroxyphenyl]methyl-4-thiazolidinone were added. The resulting solution was cooled to −20° C. and 0.73 ml (1.88 mmol) of a 2.57M solution of t-butylhydroperoxide in isooctane were added. The reaction solution was then stirred for 6 hours at −20° C.

After 6 hours, the reaction solution was quenched by pouring it into 50 ml of a solution prepared from 9.9 g of Iron (II) sulfate heptahydrate, 3.3 g of citric acid monohydrate and water. The resulting solution was stirred for 30 minutes and then stirring was stopped so that the organic and aqueous layers could separate. The aqueous layer was decanted and washed with methylene chloride. The methylene chloride wash was combined with the above organic layer and the resulting solution was washed with a saturated brine solution and then dried over sodium sulfate. The sodium sulfate was removed by filtration and the remaining liquid was evaporated to provide 1.81 g of a residue.

The residue was dissolved in 25 ml of methylene chloride and the resulting solution was chromatographed on a silica gel chromatography column. Elution with 6000 ml of a 10-50% ethyl acetate in hexane gradient provided various fractions containing the above titled compound. These fractions were combined and the liquid evaporated to provide 0.19 g of title compound. $[\alpha]^{25}= -73.6°$ (C=1.0, MeOH).

Analysis for $C_{18}H_{27}NO_2S$:
Calculated: C, 67.25; H, 8,47; N, 4.36.
Found: C, 67.50; H, 8.53; N, 4.48.

EXAMPLE 25, 26 and 27

(+)-5-[[3,5-Bis(1,1-dimethylethyl)-4-hydroxyphenyl]-methyl]-4-thiazolidinone, (-)-5-[3,5-bis(1,1-dimethylethyl)-4-hydroxyphenyl]methyl]-4-thiazolidinone-1-oxide and (+)-5-[[3,5-bis(1,1-dimethylethyl)-4-hydroxyphenyl]methyl]-4-thiazolidinone-1-oxide.

In a similar manner as that described in Example 24, 0.89 ml (3.0 mmol) of titanium isopropoxide, 1.27 ml (6.0 mmol) of (-)-diisopropyl tartrate, 54 μl (3.0 mmol) of deionized water, 1.61 g (5.0 mmol) of racemic 5-[[3,5-bis(1,1-dimethylethyl)-4-hydroxyphenyl]methyl-4-thiazolidinone and 2.4 ml (6.5 solution of t-butylhydroperoxide in isooctane were reacted to provide a residue. The residue was dissolved in 75 ml of methylene chloride and the resulting solution was chromatographed on a silica gel chromatography column. Elution with 6000 ml of a 10-50% ethyl acetate in hexane gradient provided various fractions containing (+)-5-[[3,5-bis(1,1-dimethylethyl)-4-hydroxyphenyl]methyl-4-thiazolidinone. These fractions were combined and the liquid evaporated to provide 0.43 g of product compound. Further elution with 4000 ml of a 50% isopropanol in hexane solution provided various fractions. Fractions believed to contain (-)-5-[[3,5-bis(1,1-dimethylethyl)-4-hydroxyphenyl]methyl]-4-thiazolidinone-1-oxide were combined and the liquid evaporated to provide 0.87 g of product. Fractions believed to contain (+)-5-[[3,5bis(1,1-dimethylethyl)-4-hydroxyphenyl]methyl]-4-thiazolidinone-1-oxide were combined and the liquid evaporated to provide 0.27 g of product.

25.   (+)-5-[[3,5-bis(1,1-dimethylethyl)-4-hydroxyphenyl]methyl]-4-thiazolidinone
$[\alpha]^{25}= +70.41°$ (c=1.0, MeOH).
Analysis for $C_{18}H_{27}NO_2S$:
Calculated: C, 67.25; H, 8.47; N, 4.36.
Found: C, 66.95; H, 8.22; N, 4.26.

26.   (−)-5-[[3,5-bis(1,1-dimethylethyl)-4-hydroxyphenyl]methyl]-4-thiazolidinone-1-oxide  m.p. 182°–184° C.
$[\alpha]^{25}= -21.84°$ (c=1.0, MeOH).
Analysis for $C_{18}H_{27}NO_3S$:
Calculated: C, 64.06; H, 8.06; N, 4.15.
Found: C, 63.84; H, 8.09; N, 4.12.

27.   (+)-5-[[3,5-bis(1,1-dimethylethyl)-4-hydroxyphenyl]methyl]-4-thiazolidinone-1-oxide  m.p. 177°–181° C.
$[\alpha]^{25}= +163.05°$ (c=1.0, MeOH).
Analysis for $C_{18}H_{27}NO_3S$:
Calculated: C, 64.06; H, 8.06; N, 4.15.
Found: C, 63.88; H, 8.12; N, 4.29.

EXAMPLE 28

(−)-5-[[3,5-Bis(1,1-dimethylethyl)-4-hydroxyphenyl]-phenyl]methyl]-3-methyl-4-thiazolidinone In a similar manner as that described in Example 24, 0.45 ml (1.5 mmol) of titanium isopropoxide, 0.63 ml (3.0 mmol) of (+)-diisopropyltartrate, 27 μl (1.5 mmol) of water, 0.84 g (2.5 mmol) of racemic 5-[[3,5-bis(1,1-dimethylethyl)-4-hydroxyphenyl]methyl]-3-methyl-4-thiazolidinone and 0.58 ml (1.5 mmol) of a 2.57M solution of t-butylhydroperoxide in isooctane were reacted to provide a residue. The residue was dissolved in 25 ml of methylene chloride and the resulting solution was chromatographed on a silica gel chromatography column. Elution with 1000 ml of methylene chloride, then 6000 ml of a 0-10% ethyl acetate in methylene chloride gradient, then 4000 ml of a 20-50% isopropyl alcohol in hexane gradient and then 2000 ml of a 50% isopropyl alcohol/hexane solution provided various fractions containing the above-titled compound. These fractions were combined and the liquid evaporated to provide 0.35 g of title compound.

Analysis for $C_{19}H_{29}NO_2S$:
Calculated: C, 68.02; H, 8.71; N, 4.17.
Found: C, 67.95; H, 8.55; N, 4.18.
NMR (300 MHz; $CDCl_3$)δ=1.4 (s, 18H), 2.9 (s, 3H), 3.0 (dd, 1H), 3.3 (dd, 1H), 3.8 (dd, 1H), 4.0 (d, 1H), 4.2 (d, 1H), 5.1 (s, 1H), 7.1 (s, 2H).

The present invention provides a method of treating inflammatory bowel disease in mammals. Such activity was demonstrated in the following test system.

Sprague-Dawley rats from Charles River Laboratories, Portage, Mich. (either sex, weight approximately 250 g) were dosed orally twice a day with test compound (10 mg/kg) or vehicle (control) for three days. On the third day, the rats were given an intracolonic enema of 2% acetic acid via a cannula, the tip of which was placed 8 cm above the anal verge. This concentration of acetic acid produced a severe inflammatory response in the colon characterized by rectal bleeding, diarrhea, epithelial erosions and destructions of crypts and gland cells. Twenty-four hours later the test and control animals were killed and the distal ten centimeters of the colon were removed and opened longitudinally. The tissue lesions contained within the removed, opened, section of colon were scored by three independent, blinded observers on a scale of 0 to 4 (zero = normal, four = worst inflammation). In each test group 5–7 rats were used. The results of such testing are reported in Table I, below.

TABLE I

Inhibition of Acetic Acid Induced Colitis

| Compound of Example No. | Lesion Score |
| --- | --- |
| Control | 3.4 ± 0.3 |
| Example 1 | 2.2 ± 0.5 |
| Example 2 | 1.1 ± 0.5 |
| Example 3 | 0.4 ± 0.1 |
| Example 4 | 1.5 ± 0.3 |
| Example 6 | 2.4 ± 0.5 |
| Example 7 | 2.1 ± 0.1 |
| Example 9 | 2.2 ± 0.5 |
| Example 10 | 1.2 ± 0.3 |
| Example 11 | 2.4 ± 0.7 |
| Example 12 | 2.0 ± 0.6 |
| Example 16 | 1.2 ± 0.5 |
| Example 18 | 2.8 ± 0.5 |
| Example 21 | 1.5 ± 0.5 |
| Example 22 | 0.8 ± 0.2 |
| Example 23 | 2.7 ± 0.6 |
| Example 24 | 1.0 ± 0.2 |
| Example 25 | 2.5 ± 0.7 |
| Example 26 | 2.4 ± 0.6 |
| Example 27 | 2.2 ± 0.5 |

Spraque-Dawley rats from Charles River Laboratories, Portage, Mich. (male, weight approximately 300 g) were fasted for 24 hours. After 24 hours, the test animals were dosed orally with 3 ml/kg of rat weight of vehicle (control) or test compound dissolved in vehicle. Thirty minutes later each animal was given a solution consistency of 100% ethanol. Sixty minutes after ethanol administration, all animals were killed and their stomachs were removed and washed. The tissue lesions contained within the removed, opened, stomach were scored by three independent, blinded observers on a scale of 0 to 5 (zero = normal, 5 = severe damage). In each test group, six rats were employed. Test results from animals given test compound dissolved in vehicle were compared with test results from animals given vehicle alone in order to determine the percentage of lesion inhibition attributable to the test compound. The results of such testing are reported in Table II below.

TABLE II

Inhibition of Ethanol Induced Injury

| Compound of Example No. | Dose (mg/kg of rat weight) | % Inhibition |
| --- | --- | --- |
| 3 | 0.7 | 24 |
| 3 | 1.00 | 35 |
| 3 | 3.00 | 47 |
| 3 | 7.00 | 61 |
| 9 | 0.7 | 9 |
| 9 | 1.00 | 13 |
| 9 | 3.00 | 34 |
| 9 | 7.50 | 40 |
| 9 | 10.00 | 24 |
| 10 | 0.07 | 34 |
| 10 | 0.3 | 57 |
| 10 | 0.7 | 55 |
| 10 | 1.00 | 32 |

TABLE II-continued

Inhibition of Ethanol Induced Injury

| Compound of Example No. | Dose (mg/kg of rat weight) | % Inhibition |
| --- | --- | --- |
| 10 | 3.00 | 11 |

The data in Tables I and II establish that the compounds used in the method of the present invention can treat inflammatory bowel disease. The term "inflammatory bowel disease", as used for purposes of the present invention, means any disorder of the digestive system which is characterized by inflammation. Examples of such disorders include Crohn's disease, mucous colitis, ulcerative colitis, psuedomembranous enterocolitis, non-specific colonic ulcers, collagenous colitis, cathartic colon, ulcerative proctitis, radiation enteritis and colitis, idiopathic diffuse ulcerative nongranulamatus enteritis, nonsteroidal antiinflammatory drug induced inflammations, celic sprue, gastritis and the like.

The method of the present invention comprises administering to a mammal suffering from inflammatory bowel disease an effective amount of one or more of the compounds of Formula I. Administration may be done either therapeutically or prophylactically and is accomplished by means of pharmaceutical compositions which are prepared by techniques well known in the pharmaceutical sciences.

The compounds of Formula I are effective over a wide dosage range in treating inflammatory bowel disease. Thus, as used herein, the term "effective amount" refers to a dosage range of from about 0.001 to about 200 mg/kg of body weight per day. In the treatment of adult humans, the range of about 0.1 to about 50 mg/kg, in single or divided doses, is preferred. However, it will be understood that the amount of compound actually administered will be determined by a physician in light of the relevant circumstances, including the condition to be treated, the choice of compound to be administered, the chosen route of administration, the age, weight, and response of the individual patient, and the severity of the patient's symptoms. Therefore, the above dosage ranges are not intended to limit the scope of the invention in any way.

While the compounds of Formula I are preferably administered orally or intrarectally, the compounds may also be administered by a variety of other routes such as the transdermal, subcutaneous, intranasal, intramuscular and intravenous routes.

The present invention provides new compounds of Formula II which are also useful in treating inflammatory bowel disease. Accordingly, the present invention is also directed to pharmaceutical compositions which include at least one compound of Formula II in association with one or more pharmaceutically acceptable diluents, excipients or carriers therefor.

In making the pharmaceutical compositions of the present invention, one or more compounds of Formula II will usually be mixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of active compound, soft and hard gelatin capsules, suppositories, sterile injectable solutions and sterile packaged powders.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, methyl cellulose, methyl- and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide rapid, sustained or delayed release of the active ingredient after administration to the patient by employing procedures well known in the art.

The compositions are formulated, preferably in a unit dosage form, such that each dosage contains from about 5 to about 500 mg, more usually about 25 to about 300 mg, of the active ingredient. The term "unit dosage form" refers to physically discrete units suitable as unitary dosages for human subjects and other mammals, each unit containing a predetermined quantity of active material calculated to produce the desired therapeutic effect, in association with one or more suitable pharmaceutical diluents, excipients or carriers.

The following formulation examples may employ as active ingredients any of the compounds of Formula II. The examples are illustrative only and are not intended to limit the scope of the invention in any way.

EXAMPLE 29

Hard gelatin capsules are prepared using the following ingredients:

|  | Quantity (mg/capsule) |
| --- | --- |
| Compound of Example 11 | 250 |
| Starch dried | 200 |
| Magnesium stearate | 10 |

The above ingredients are mixed and filled into hard gelatin capsules in 460 mg quantities.

EXAMPLE 30

A tablet formula is prepared using the ingredients below:

|  | Quantity (mg/tablet) |
| --- | --- |
| Compound of Example 11 | 250 |
| Cellulose, microcrystalline | 400 |
| Silicon dioxide, fumed | 10 |
| Stearic acid | 5 |

The components are blended and compressed to form tablets each weighing 665 mg.

EXAMPLE 31

An aerosol solution is prepared containing the following components:

|  | Weight % |
| --- | --- |
| Compound of Example 12 | 0.25 |
| Ethanol | 29.75 |
| Propellant 22 | 70.00 |

|  | Weight % |
| --- | --- |
| (Chlorodifluoromethane) |  |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

EXAMPLE 32

Tablets each containing 60 mg of active ingredient are made up as follows:

| Compound of Example 12 | 60 mg |
| --- | --- |
| Starch | 45 mg |
| Microcrystalline cellulose | 35 mg |
| Polyvinylpyrrolidone | 4 mg |
| (as 10% solution in water) |  |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°-60° C. and passed through a No. 18 mesh U.S. sieve. The sodium carboxymethyl starch, magnesium stearate and talc, previously passed through a No. 60 mesh U.S. sieve, are then added to the granules which, after mixing, are compressed by a tablet machine to yield tablets each weighing 150 mg.

EXAMPLE 33

Capsules each containing 80 mg of medicament are made as follows:

| Compound of Example 12 | 80 mg |
| --- | --- |
| Starch | 59 mg |
| Microcrystalline cellulose | 59 mg |
| Magnesium stearate | 2 mg |
| Total | 200 mg |

The active ingredient, cellulose, starch and magnesium stearate are blended, passed through a No. 45 mesh U.S. sieve, and filled into hard gelatin capsules in 200 mg quantities.

EXAMPLE 34

Suppositories each containing 225 mg of active ingredient are made as follows:

| Compound of Example 13 | 225 mg |
| --- | --- |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

EXAMPLE 35

Suspensions each containing 50 mg of medicament per 5 ml dose are made as follows:

| | |
|---|---|
| Compound of Example 11 | 50 mg |
| Sodium carboxymethylcellulose | 50 mg |
| Syrup | 1.25 ml |
| Benzoic acid solution | 0.10 ml |
| Flavor | q.v. |
| Color | q.v. |
| Purified water to | 5 ml |

The medicament is passed through a No. 45 mesh U.S. sieve and mixed with the sodium carboxymethyl cellulose and syrup to form a smooth paste. The benzoic acid solution, flavor and color are diluted with some of the water and added, with stirring. Sufficient water is then added to produce the required volume.

EXAMPLE 36

Capsules each containing 150 mg of medicament are made as follows:

| | |
|---|---|
| Compound of Example 13 | 150 mg |
| Starch | 164 mg |
| Microcrystalline cellulose | 164 mg |
| Magnesium stearate | 22 mg |
| Total | 500 mg |

The active ingredient, cellulose, starch and magnesium stearate are blended, passed through a No. 45 mesh U.S. sieve, and filled into hard gelatin capsules in 500 mg quantities.

We claim:

1. A method of treating inflammatory bowel disease in a mammal suffering from said disease, or susceptible to said disease, comprising administering to said mammal an effective amount of a compound of Formula I

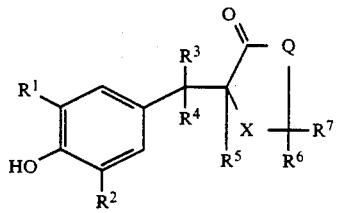

wherein:

$R^1$ and $R^2$ are each independently hydrogen, $C_1$-$C_6$ alkyl, $C_1$-$C_6$ alkoxy, $C_2$-$C_6$ alkenyl, $C_2$-$C_6$ alkynyl,

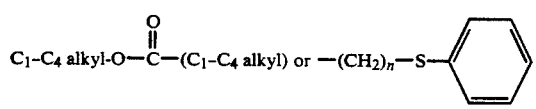

where n is an integer from 0 to 3, both inclusive;

$R^3$ is hydrogen or $C_1$-$C_6$ alkyl;

$R^4$ and $R^5$ are each hydrogen or when taken together form a bond;

$R^6$ and $R^7$ are each hydrogen or when taken together are =S, or when one of $R^6$ and $R^7$ is hydrogen the other is —OH or —SCH$_3$;

X is

where m is 0, 1 or 2; and

Q is —CH$_2$—, —O— or NR$^8$ where R$^8$ is hydrogen, $C_1$-$C_6$ alkyl, $C_2$-$C_6$ alkenyl, $C_3$-$C_8$ cycloalkyl, —SO$_2$CH$_3$ or —(CH$_2$)$_n$—Y, where n is an integer from 0 to 3, both inclusive, and Y is cyano, OR$^9$,

tetrazolyl, —NR$^{11}$R$^{12}$, —SH, —S($C_1$-$C_4$ alkyl) or

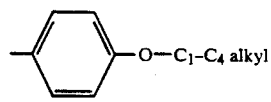

where $R^9$ is hydrogen, $C_1$-$C_4$ alkyl, or

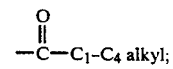

$R^{10}$ is $C_1$-$C_4$ alkyl, $C_1$-$C_4$ alkoxy or —NH$_2$; $R^{11}$ and $R^{12}$ are each independently hydrogen, $C_1$-$C_6$ alkyl, $C_2$-$C_6$ alkenyl, $C_2$-$C_6$ alkynyl, —(CH$_2$)$_q$OH, —(CH$_2$)$_q$—N($C_1$-$C_4$ alkyl)$_2$, —(CH$_2$)$_q$—S($C_1$-$C_4$ alkyl) or

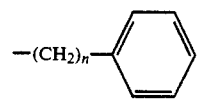

where n is as defined above and q is an integer from 1 to 6, both inclusive; or $R^{11}$ and $R^{12}$ taken together form a morpholinyl, piperidinyl, piperazinyl or N-methylpiperazinyl ring; or a pharmaceutically acceptable salt thereof.

2. A method of claim 1 wherein a compound of Formula I wherein $R^1$ and $R^2$ are each $C_1$-$C_6$ alkyl, $C_2$-$C_6$ alkenyl, $C_1$-$C_6$ alkoxy or

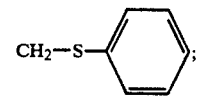

$R^3$ is hydrogen; $R^4$ and $R^5$ are each hydrogen or when taken together form a bond; $R^6$ and $R^7$ are each hydrogen or when taken together are =S; X is

where m is 0; and Q is —O— or NR$^8$, where R$^8$ is as defined in claim 1, or a pharmaceutically acceptable salt thereof, is employed.

3. A method of claim 2 wherein a compound of Formula I wherein $R^1$, $R^2$, $R^3$, $R^4$, $R^5$, $R^6$, $R^7$, X and m are as defined in claim 2; and Q is NR$^8$ where R$^8$ is hydrogen, $C_1$-$C_6$ alkyl or —(CH$_2$)$_n$—Y; where n is 0 and Y is —NR$^{11}$R$^{12}$ (R$^{11}$ and R$^{12}$ each being independently hydrogen or C$_1$-C$_6$ alkyl), or a pharmaceutically acceptable salt thereof, is employed.

4. A method of claim 3 wherein a compound of Formula I wherein R: and R$^2$ are each independently C$_1$-C$_6$ alkyl; R$^3$, R$^4$, R$^5$, R$^6$ and R$^7$ are hydrogen; X is

where m is 0; and Q is NR$^8$ where R$^8$ is hydrogen, or a pharmaceutically acceptable salt thereof, is employed.

5. A method of claim 4 wherein a compound of Formula I wherein one of R or R$^2$ is 1,1-dimethylethyl and the other is a C$_1$-C$_6$ alkyl other than 1,1-dimethylethyl; R$^3$, R$^4$, R$^5$, R$^6$ and R$^7$ are hydrogen; X is

where m is 0; and Q is NR$^8$ where R$^8$ is hydrogen, or a pharmaceutically acceptable salt thereof, is employed.

6. The method of claim 5 which employs 5-[[3-(1,1-dimethylethyl)-4-hydroxy-5-propylphenyl]methyl]-4-thiazolidinone.

7. The method of claim 4 which employs 3,5-bis(1,1-dimethylethyl)-4-hydroxyphenyl]methyl]-4-thiazolidinone.

8. The method of claim 4 which employs 5-[[3,5-dipropyl-4-hydroxyphenyl]methyl]-4-thiazolidinone.

9. A compound of the formula

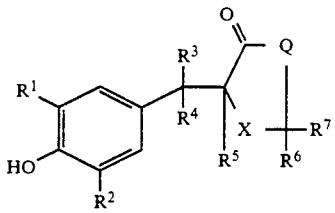

wherein:
R$^1$ is C$_2$-C$_6$ alkenyl; C$_2$-C$_6$ alkynyl or

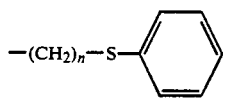

where n is an integer from 0 to 3, both inclusive;
R$^2$ is hydrogen, C$_1$-C$_6$ alkyl, C$_1$-C$_6$ alkoxy, C$_2$-C$_6$ alkenyl, C$_2$-C$_6$ alkynyl,

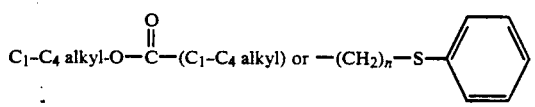

where n is an integer from 0 to 3, both inclusive:
R$^3$ is hydrogen or C$_1$-C$_6$ alkyl;
R$^4$ and R$^5$ are each hydrogen or when taken together form a bond;
R$^6$ and R$^7$ are each hydrogen or when taken together are =S, or when one of R$^6$ and R$^7$ is hydrogen the other is —OH or —SCH$_3$;

X is

where m is 0, 1 or 2; and
Q is —CH$_2$—, —O— or NR$^8$ where R$^8$ is hydrogen, C$_1$-C$_6$ alkyl, C$_2$-C$_6$ alkenyl, C$_3$-C$_8$ cycloalkyl, —SO$_2$CH$_3$ or —(CH$_2$)$_n$—Y, where n is an integer from 0 to 3, both inclusive, and Y is cyano, OR$^9$,

tetrazolyl, —NR$^{11}$R$^{12}$, —SH, —S(C$_1$-C$_4$ alkyl) or

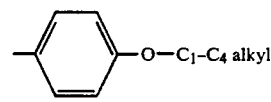

where R$^8$ is hydrogen, C$_1$-C$_4$ alkyl, or

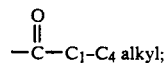

R$^{10}$ is C$_1$-C$_4$ alkyl, C$_1$-C$_4$ alkoxy or —NH$_2$; R$^{11}$ and R$^{12}$ are each independently hydrogen, C$_1$-C$_6$ alkyl, C$_2$-C$_6$ alkenyl, C$_2$-C$_6$ alkynyl, —(CH$_2$)$_q$OH, —(CH$_2$)$_q$—N(C$_1$-C$_4$ alkyl)$_2$, —(CH$_2$)$_q$—S(C$_1$-C$_4$ alkyl) or

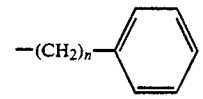

where n is as defined above and q is an integer from 1 to 6, both inclusive; or R$^{11}$ and R$^{12}$ taken together form a morpholinyl, piperidinyl, piperazinyl or N-methylpiperazinyl ring; or a pharmaceutically acceptable salt thereof.

10. A compound of claim 9 wherein R$^1$ is C$_2$-C$_6$ alkenyl; R$^2$ is C$_2$-C$_6$ alkenyl or C$_1$-C$_6$ alkyl; R$^3$ is hydrogen; R$^4$ and R$^5$ are hydrogen or when taken together form a bond; R$^6$ and R$^7$ are each hydrogen or when taken together are =S; X is

where m is 0; and Q is —O— or NR$^8$, where R$^8$ is as in claim 9, and pharmaceutically acceptable salts thereof.

11. A compound of claim 10 wherein Q is NR$^8$ where R$^8$ is hydrogen, C$_1$-C$_6$ alkyl or —(CH$_2$)$_n$—Y, where n is 0 and Y is NR$^{11}$R$^{12}$ where R$^{11}$ and R$^{12}$ are each independently hydrogen or C$_1$-C$_6$ alkyl, and pharmaceutically acceptable salts thereof.

12. A compound of claim 11 wherein R$^1$ and R$^2$ are each independently C$_2$-C$_6$ alkenyl; R$^3$, R$^4$, R$^5$, R$^6$ and R$^7$ are each hydrogen; X is

where m is 0; and Q is $NR^8$ where $R^8$ is hydrogen, and pharmaceutically acceptable salts thereof.

13. The compound of claim 12 which is 5-[[3,5-di-2-propenyl-4-hydroxyphenyl]methyl]-4-thiazolidinone and pharmaceutically acceptable salts thereof.

14. A pharmaceutical composition comprising an effective amount of a compound of claim 9, or a pharmaceutically acceptable salt thereof, in association with one or more pharmaceutically acceptable diluents, excipients or carriers therefor.

15. A process for selectively isolating, in substantially pure enantiomeric form, one of the enantiomers of a racemic mixture of a compound of the formula

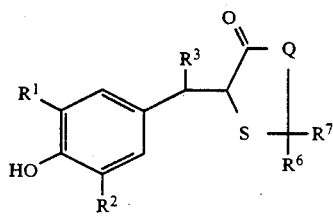

wherein:

$R^1$ and $R^2$ are each independently hydrogen, alkyl, $C_1$-$C_6$ alkoxy, $C_2$-$C_6$ alkenyl, $C_2$-$C_6$ alkynyl,

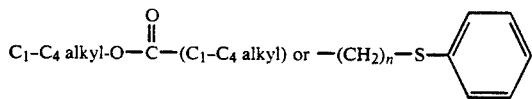

where n is an integer from 0 to 3, both inclusive;
$R^3$ is hydrogen or $C_1$-$C_6$ alkyl;
$R^6$ and $R^7$ are each hydrogen or when taken together are =S, or when one of $R^6$ and $R^7$ is hydrogen the other is —OH or —$SCH_3$;
Q is —$CH_2$—, —O— or $NR^8$ where $R^8$ is hydrogen, $C_1$-$C_6$ alkyl, $C_2$-$C_6$ alkenyl, $C_3$-$C_8$ cycloalkyl, —$SO_2CH_3$ or —$(CH_2)_n$—Y, where n is an integer from 0 to 3, both inclusive, and Y is cyano, $OR^9$,

tetrazolyl, —$NR^{11}R^{12}$, —SH, —$S(C_1$-$C_4$ alkyl) or

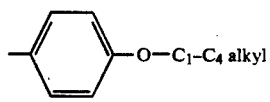

where $R^9$ is hydrogen, $C_1$-$C_4$ alkyl or

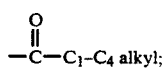

$R^{10}$ $C_1$-$C_4$ alkyl, $C_1$-$C_4$ alkoxy or —$NH_2$; $R^{11}$ and $R^{12}$ are each independently hydrogen, $C_1$-$C_6$ alkyl, $C_2$-$C_6$ alkenyl, $C_2$-$C_6$ alkynyl, —$(CH_2)_qOH$, —$(CH_2)_q$—$N(C_1$-$C_4$ alkyl$)_2$, —$(CH_2)_q$—$S(C_1$-$C_4$ alkyl) or

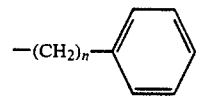

where n is as defined above and q is an integer from 1 to 6, both inclusive; or $R^{11}$ and $R^{12}$ taken together form a morpholinyl, piperidinyl, piperazinyl or N-methylpiperazinyl ring, comprising:

a) reacting the racemic sulfide compound with a reagent prepared from the combination of a tartrate ligand, a titanium alkoxide, a hydroperoxide and, optionally, water until substantially all of the undesired enantiomer of the sulfide substrate has been converted to its sulfoxide analog; and b) separating the unreacted portion of the sulfide starting material, consisting essentially of substantially pure desired enantiomer, from the reaction mixture.

16. A process of claim 15 which employs as starting material a racemic sulfide compound wherein $R^1$ and $R^2$ are each $C_1$-$C_6$ alkyl, $C_2$-$C_6$ alkenyl, $C_1$-$C_6$ alkoxy or

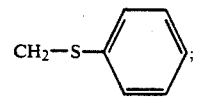

$R^3$, $R^6$ and $R^7$ are hydrogen; and Q is $NR^8$ where $R^8$ is hydrogen, $C_1$-$C_6$ alkyl or —$(CH_2)_n$—Y where n is 0 and Y is $NR^{11}R^{12}$ ($R^{11}$ and $R^{12}$ each being independently hydrogen or $C_1$-$C_6$ alkyl).

17. A process of claim 16 which employs Ti(O-isopropyl)$_4$ as the titanium alkoxide.

18. A process of claim 16 which employs diisopropyl tartrate as the tartrate ligand.

19. A process of claim 16 which employs t-butylhydroperoxide as the hydroperoxide.

20. A process of claim 17 which employs diisopropyl tartrate as the tartrate ligand.

21. A process of claim 17 which employs t-butylhydroperoxide as the hydroperoxide.

22. A process of claim 18 which employs t-butylhydroperoxide as the hydroperoxide.

23. A process of claim 20 which employs t-butylhydroperoxide as the hydroperoxide.

24. A process of claim 16 which employs as starting material racemic. 5-[[3,5-bis(1,1-dimethylethyl)-4-hydroxyphenyl]methyl]-4-thiazolidinone and reacts that compound with a reagent prepared from the combination of Ti(O-isopropyl)$_4$, (—)-diisopropyl tartrate, t-butylhydroperoxide and water so as to provide essentially pure (+)-5-[[3,5-bis(1,1-dimethylethyl)-4-hydroxyphenyl]methyl]-4-thiazolidinone.

25. A process of claim 16 which employs as starting material racemic 5-[[3,5-bis(1,1-dimethylethyl)-4-hydroxyphenyl]methyl]-4-thiazolidinone and reacts that compound with a reagent prepared from the combination of Ti(O-isopropyl)$_4$, (+)-diisopropyl tartrate, t-butylhydroperoxide and water so as to provide essentially pure (—)-5-[[3,5-bis(1,1-dimethylethyl)-4-hydroxyphenyl]methyl]-4-thiazolidinone.

26. The method of claim 7 which employs (−)-5-[[3,5-bis(1,1-dimethylethyl)-4-hydroxyphenyl]methyl]-4-thiazolidinone.

27. The method of claim 7 which employs (+)-5-[[3,5-bis(1,1-dimethylethyl)-4-hydroxyphenyl]methyl]-4-thiazolidinone.

28. The method of claim 7 which employs (±)-5-[[3,5-bis(1,1-dimethylethyl)-4-hydroxyphenyl]methyl]-4-thiazolidinone.

* * * * *

UNITED STATES PATENT AND TRADEMARK OFFICE
CERTIFICATE OF CORRECTION

PATENT NO. : 5,216,002

DATED : June 1, 1993

INVENTOR(S) : Jaswant S. Gidda, et al.

It is certified that an error appears in the above-identified patent and that said Letters Patent is hereby corrected as shown below:

Column 4, Line 28, delete "$C_1$-$C_4$ alkyl", and insert therefor --$C_1$-$C_6$ alkyl--.

Column 5, Line 3, delete "hydroxyphenyl]methyl]methyl]" and insert therefor --hydroxyphenyl]methyl]--.

Column 6, Line 8, delete "phenylmethylene]" and insert therefor --phenyl]methylene]--.

Column 6, Line 11, delete "5-3,5-diacetylene" and insert therefor --5-[[3,5-diacetylene--.

Column 6, Lines 15 and 16, delete "-5-methoxyphenylmethyl" and insert therefor -- -5-methoxyphenyl]methyl--.

Column 6, Lines 23 and 24, delete "-4-hydroxyphenylmethylene" and insert therefor -- -4-hydroxyphenyl]methylene--.

Column 6, Line 30, delete "5-[3.5-bis(1.1-dimethyl)-4-hydroxyphenylmethyl]", and insert therefor --5-[[3,5-bis(1,1-dimethylethyl)-4-hydroxyphenyl]methyl]---.

Column 6, Line 35, delete "methylene-4-thiazolidinone", and insert therefor --methylene]-4-thiazolidinone--.

UNITED STATES PATENT AND TRADEMARK OFFICE
CERTIFICATE OF CORRECTION

PATENT NO. : 5,216,002 cont.

DATED : June 1, 1993

INVENTOR(S) : Jaswant S. Gidda, et al.

It is certified that an error appears in the above-identified patent and that said Letters Patent is hereby corrected as shown below:

Column 6, Line 56, delete "5-(4-hydroxy-", and insert therefor --5-[(4-hydroxy- --.

Column 7, Line 5, delete "hydroxyphenylmethylene]", and insert -- hydroxyphenyl]methylene]- --.

Column 10, Line 38, delete "Formulae I" and insert therefor --Formulae I and II--.

Column 11, Line 35 delete "m=0)", and insert therefor --(i.e., m=0)--.

Column 14, Line 22, delete "-4-hydrox-ybenzaldehyde", and insert therefor --.-4-hydroxybenzaldehyde--.

Column 15, Line 2, "-4-hydroxyphenylmethyl]", and insert therefor -- -4-hydroxyphenyl]methyl]--.

Column 15, Line 13, delete "die 2,6-dimethyl", and insert therefor --diethyl 2,6-dimethyl-.

Column 16, Line 41, delete "-4-hydroxyphenylmethylene]", and insert therefor -- 4-hydroxyphenyl]methylene]--.

Column 17, Line 53, delete "hydroxyphenylmethylene]", and insert therefor -- hydroxyphenyl]methylene--

UNITED STATES PATENT AND TRADEMARK OFFICE
CERTIFICATE OF CORRECTION

PATENT NO. : 5,216,002 cont.

DATED : June 1, 1993

INVENTOR(S) : Jaswant S. Gidda, et al.

It is certified that an error appears in the above-identified patent and that said Letters Patent is hereby corrected as shown below:

Column 18, Line 5, delete "5-(3,5-Di-2-propenyl-4-hydroxyphenyl)methyl-4-", and insert therefor --5-[(3,5-Di-2-propenyl-4-hydroxyphenyl)methyl]-4- --.

Column 19, Line 48, delete "methylene-3-", and insert therefor --methylene]-3- --.

Column 20, Line 50, delete "dimethylethyl)-hydroxy", and insert --dimethylethyl)-4-hydroxy--.

Column 20, Lines 64 and 65, delete "-4-hydroxyphenylmethylene]", and insert ---4-hydroxyphenyl]-methylene]--.

Column 21, Line 58, after "compound in", add --575--.

Column 22, Line 1, delete "(1,1-dimethylethyl)-hydroxy", and insert therefor --(1,1-dimethylethyl-4-hydroxy--.

Column 22, Line 46, delete "methylene-3-dimethylamino-", and insert therefor --methylene]-3-dimethylamino- --.

Column 23, Line 3, delete "ethoxyphenylmethylene-3-dimethylamino-", and insert therefor --ethoxyphenyl]methylene]-3-dimethylamino- --.

Column 23, Line 10, delete "hydroxyphenyl", and insert therefor --hydroxyphenyl]--.

UNITED STATES PATENT AND TRADEMARK OFFICE
CERTIFICATE OF CORRECTION

PATENT NO. : 5,216,002 cont.

DATED : June 1, 1993

INVENTOR(S) : Jaswant S. Gidda, et al.

It is certified that an error appears in the above-identified patent and that said Letters Patent is hereby corrected as shown below:

Column 23, Line 15, after "(+)-diisopropyl", add --tartrate and 34 µl(1.88 mmol) of deionized water. The--.

Column 23, Line 59, after "(6.5", add --mmol) of a 2.57M--.

Claim 5, Column 31 Line 15"R or $R^2$", and insert therefor -- $R^1$ or $R^2$ --.

Claim 7, Column 31, Line 28, delete "3,5-bis", and insert therefor --5-[[3,5-bis--.

Claim 9, Column 32, Line 25 delete "$R^8$" and insert therefor --$R^9$--

Claim 15, Column 33, Line 66, after "$R^{10}$", add --is--.

Signed and Sealed this

Twentieth Day of September, 1994

Attest:

BRUCE LEHMAN

Attesting Officer

Commissioner of Patents and Trademarks